(12) United States Patent
Lange

(10) Patent No.: US 6,264,814 B1
(45) Date of Patent: Jul. 24, 2001

(54) APPARATUS AND METHOD FOR ISOLATING AND/OR ANALYZING CHARGED MOLECULES

(75) Inventor: Hans Lange, Lampertheim (DE)

(73) Assignee: Bilatec Gesellschaft zur Entwicklung, Rudolstadt (DE)

( * ) Notice: Subject to any disclaimer, the term of this patent is extended or adjusted under 35 U.S.C. 154(b) by 0 days.

(21) Appl. No.: 09/445,447

(22) PCT Filed: May 29, 1998

(86) PCT No.: PCT/EP98/03216

§ 371 Date: Dec. 14, 1999

§ 102(e) Date: Dec. 14, 1999

(87) PCT Pub. No.: WO98/58251

PCT Pub. Date: Dec. 23, 1998

(30) Foreign Application Priority Data

Jun. 14, 1997 (DE) .............................. 197 25 190

(51) Int. Cl.[7] .......................... B01D 57/02; B01D 59/42; C12Q 1/68; G01N 33/53; G01N 33/00
(52) U.S. Cl. .............................. 204/450; 204/456; 435/6; 435/7.1; 436/94
(58) Field of Search .............................. 435/6, 91.1, 183, 435/283.1, 287.1, 287.2; 436/94; 536/23.1, 24.3, 25.3; 204/450–469

(56) References Cited

U.S. PATENT DOCUMENTS

| 4,349,429 | 9/1982 | Rhodes et al. | 204/299 |
|---|---|---|---|
| 4,617,103 | 10/1986 | Lovegrove | 204/300 R |
| 5,155,361 | 10/1992 | Lindsay | 250/307 |
| 5,209,831 | 5/1993 | MacConnell | 204/299 |
| 5,296,115 | * 3/1994 | Rocklin et al. | 204/180.1 |
| 5,338,427 | 8/1994 | Shartle et al. | 204/299 |
| 5,340,449 | 8/1994 | Shukla | 204/180 |
| 5,472,584 | * 12/1995 | Rocklin et al. | 204/180 |
| 5,833,826 | * 11/1998 | Nordman | 204/452 |
| 5,938,909 | * 8/1999 | Guo et al. | 204/609 |
| 6,090,936 | * 7/2000 | Walter et al. | 536/25.4 |

FOREIGN PATENT DOCUMENTS

| 34 32 949 | 3/1986 | (DE) . |
|---|---|---|
| 41 37 628 | 12/1992 | (DE) . |
| 44 36 215 | 5/1997 | (DE) . |
| 195 41 033 | 6/1997 | (DE) . |
| 2 402 716 | 9/1977 | (FR) . |
| 92 19960 | 11/1992 | (WO) . |
| 97/34908 | 9/1997 | (WO) . |
| 97/41219 | 11/1997 | (WO) . |

* cited by examiner

Primary Examiner—W. Gary Jones
Assistant Examiner—Frank Lu
(74) Attorney, Agent, or Firm—Arent Fox Kintner Plotkin & Kahn, PLLC

(57) ABSTRACT

Apparatus to isolate and/or analyze charged biomolecules, preferably nucleic acids, comprising: a vessel made substantially of a rigid plastic comprising a receiving chamber to receive reagents, this receiving chamber being externally accessible through an access aperture of the vessel, further two electrodes which can be moved into the receiving chamber to be in contact with the reagents, further comprising, according to the invention: a tube unit made of electrically non-conducting plastic and of such dimensions and/or being designed and/or affixable in such a way that at least part of its inside surface can be made to contact reagents and/or samples contained in the receiving chamber, the tube unit and one of the electrodes being so configured that this electrode can be brought into contact in the tube unit with reagents and/or samples. The apparatus of the invention is especially suitable to carry out methods to isolate and/or analyze charged biomolecules.

26 Claims, 27 Drawing Sheets

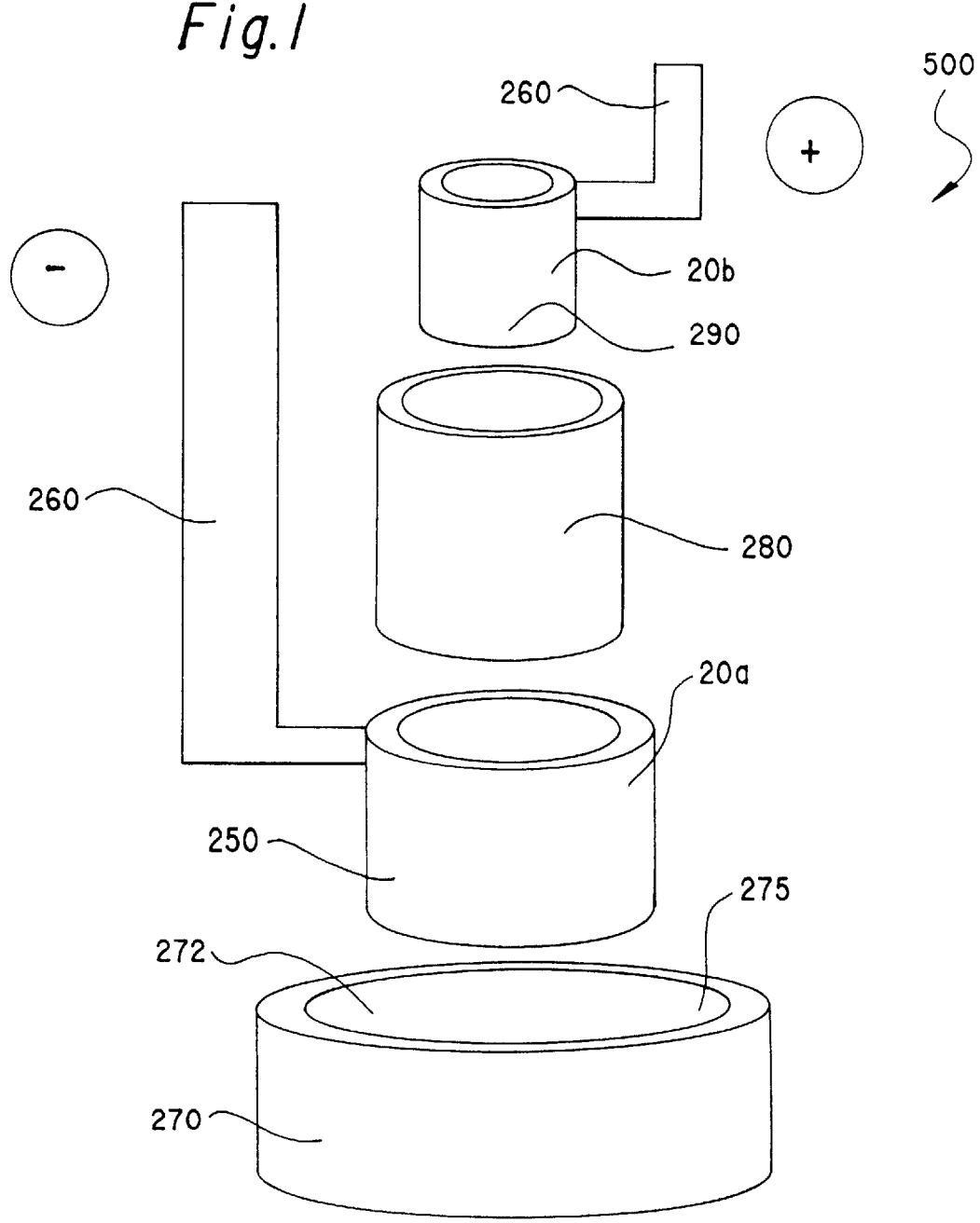

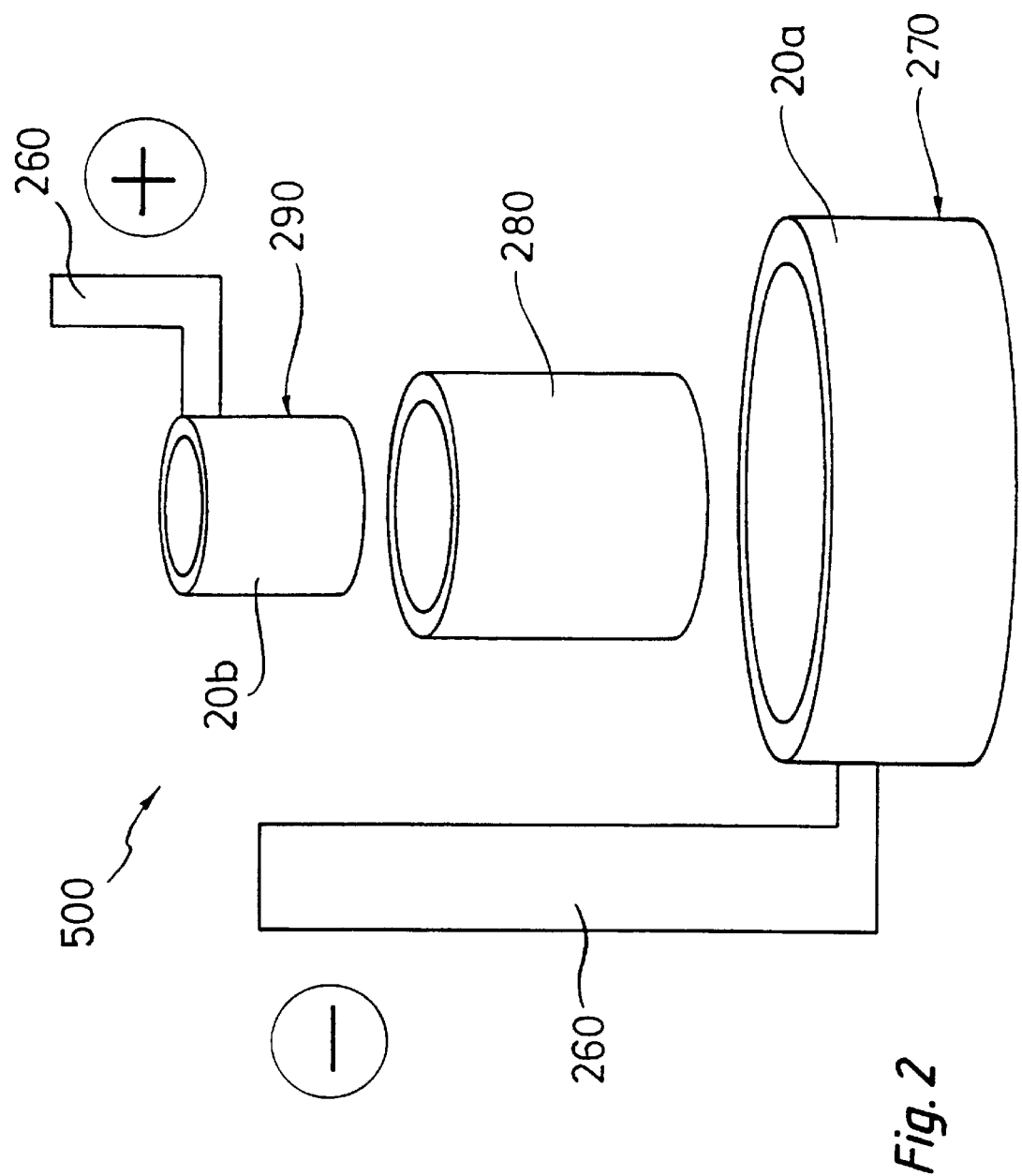

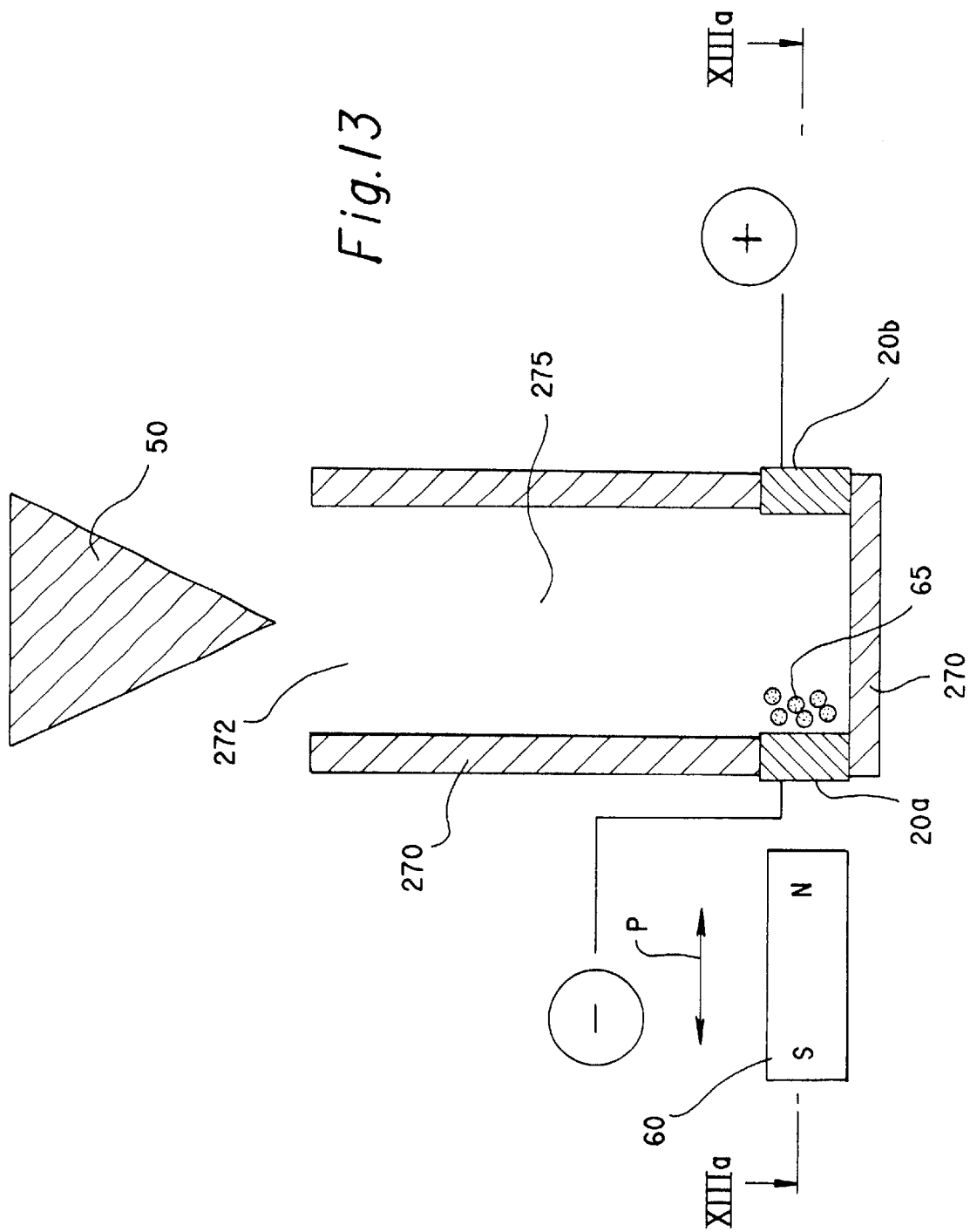

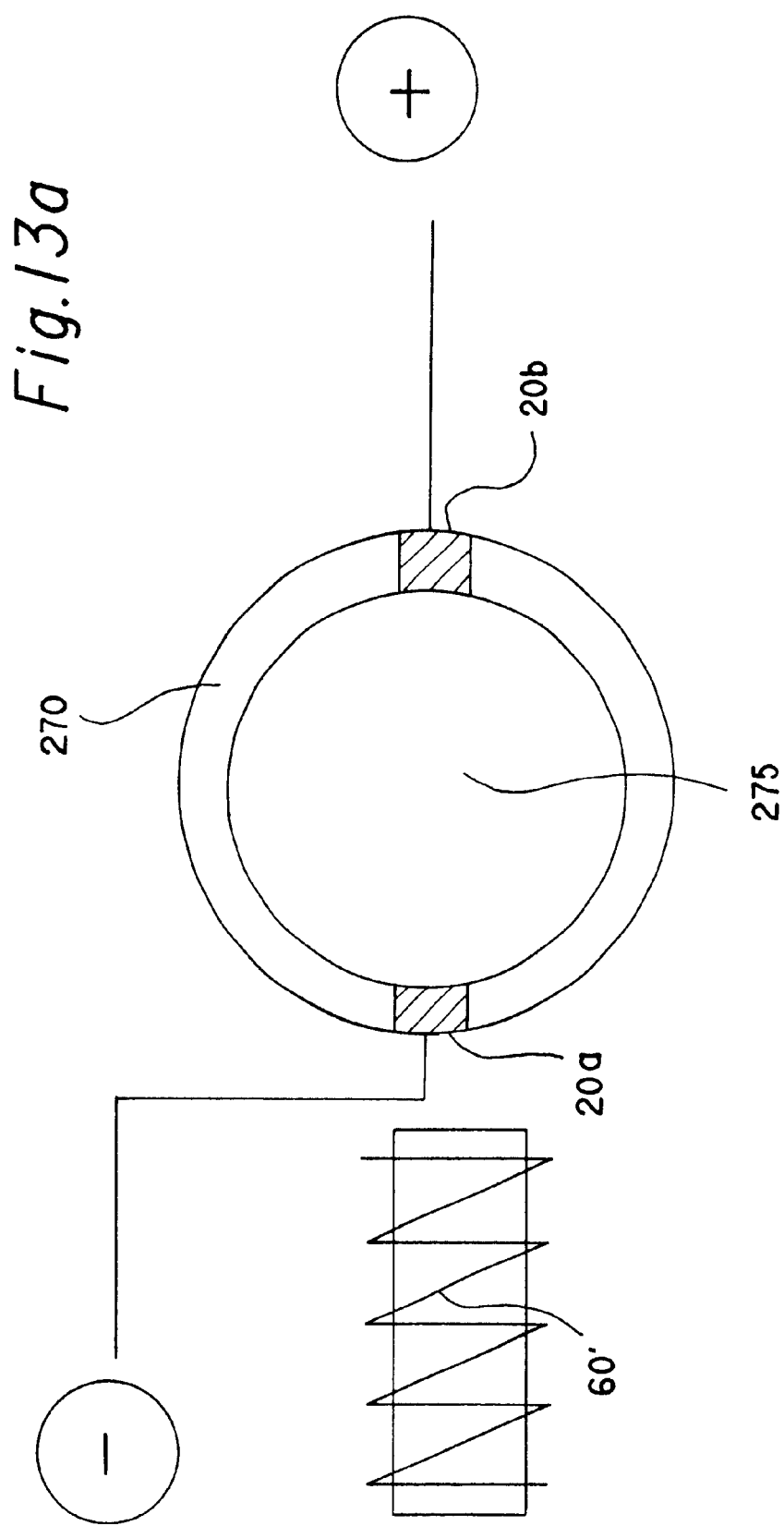

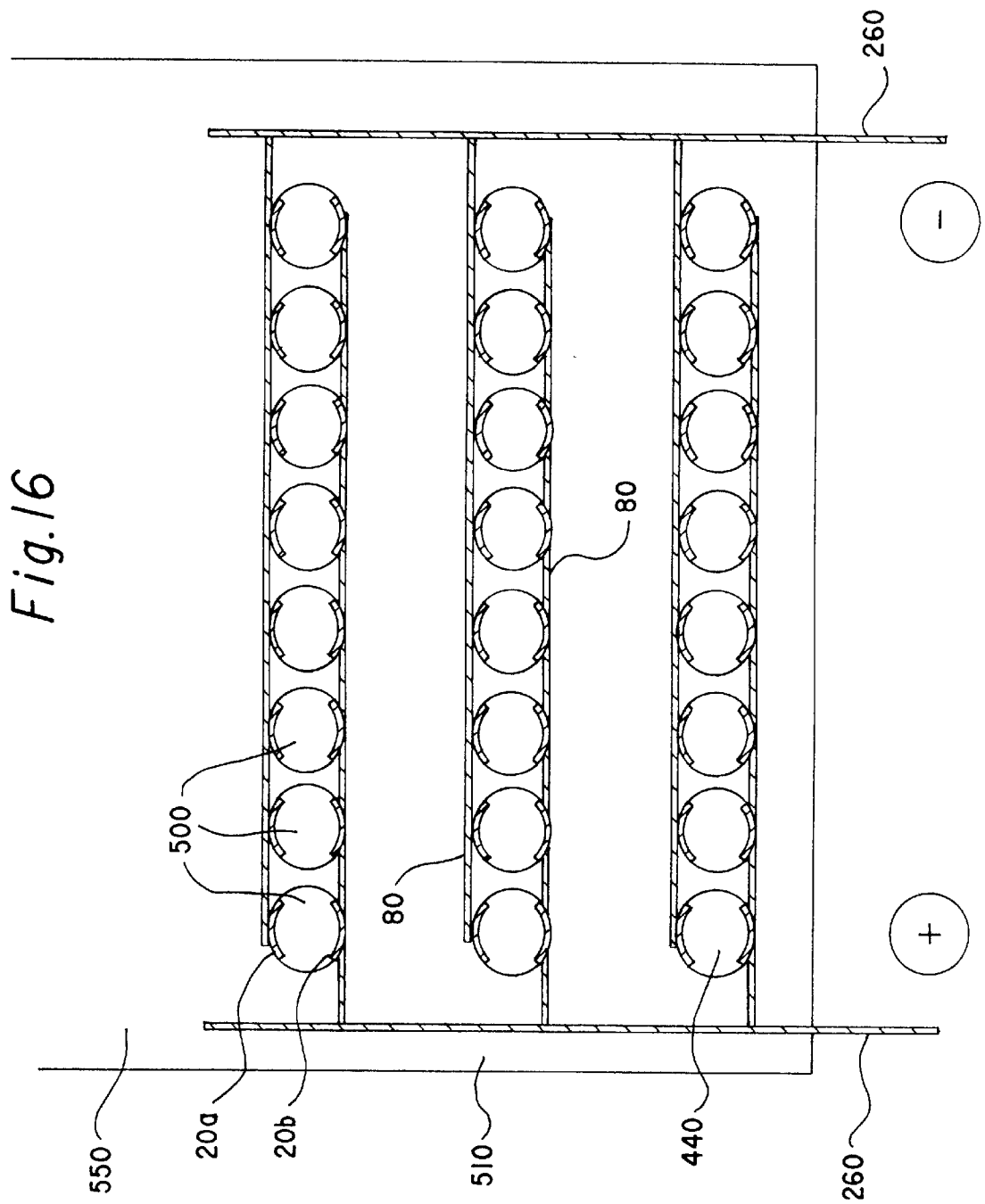

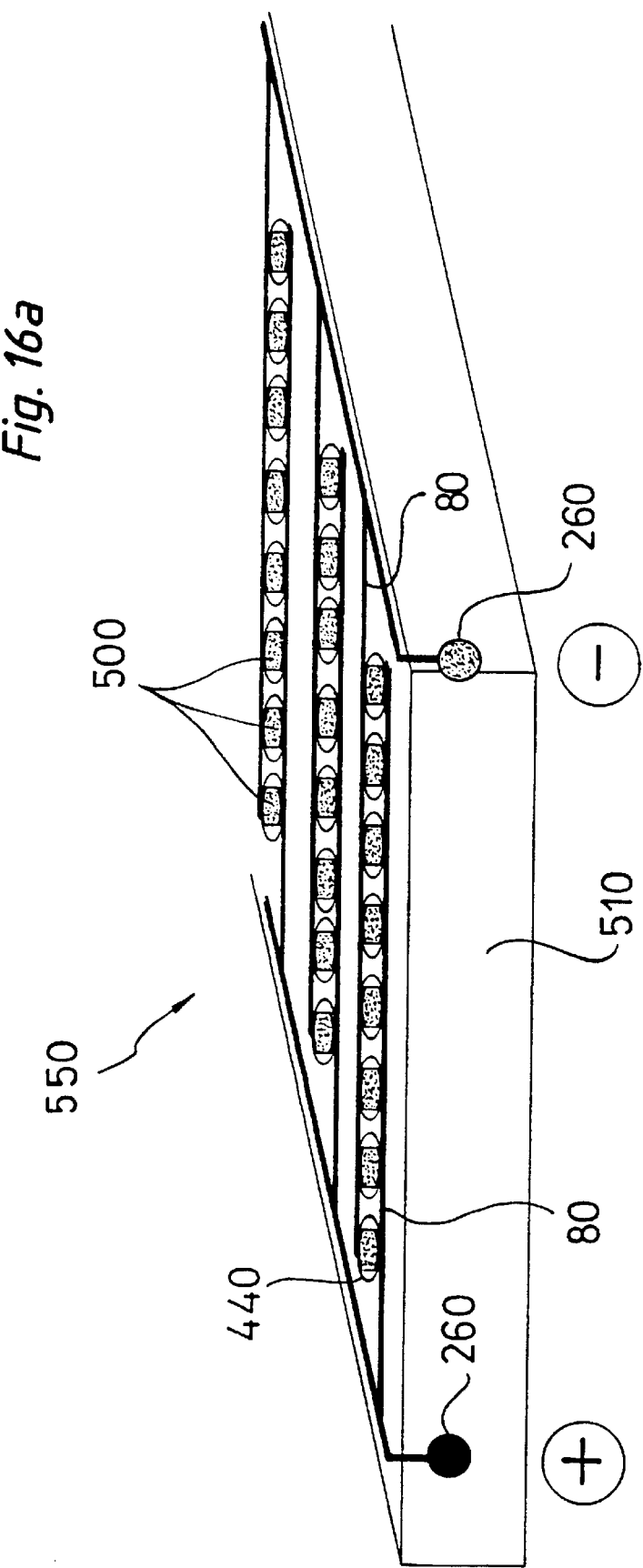

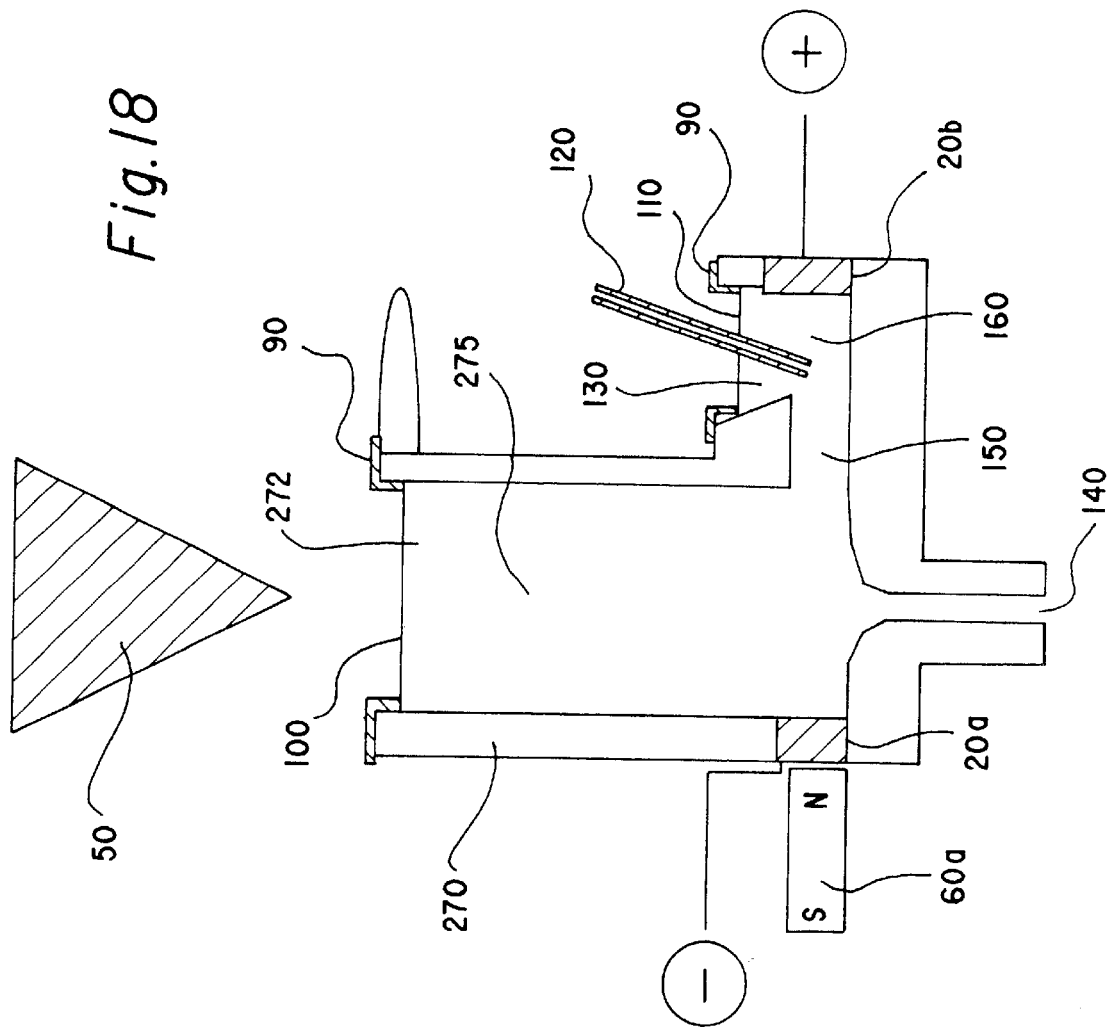

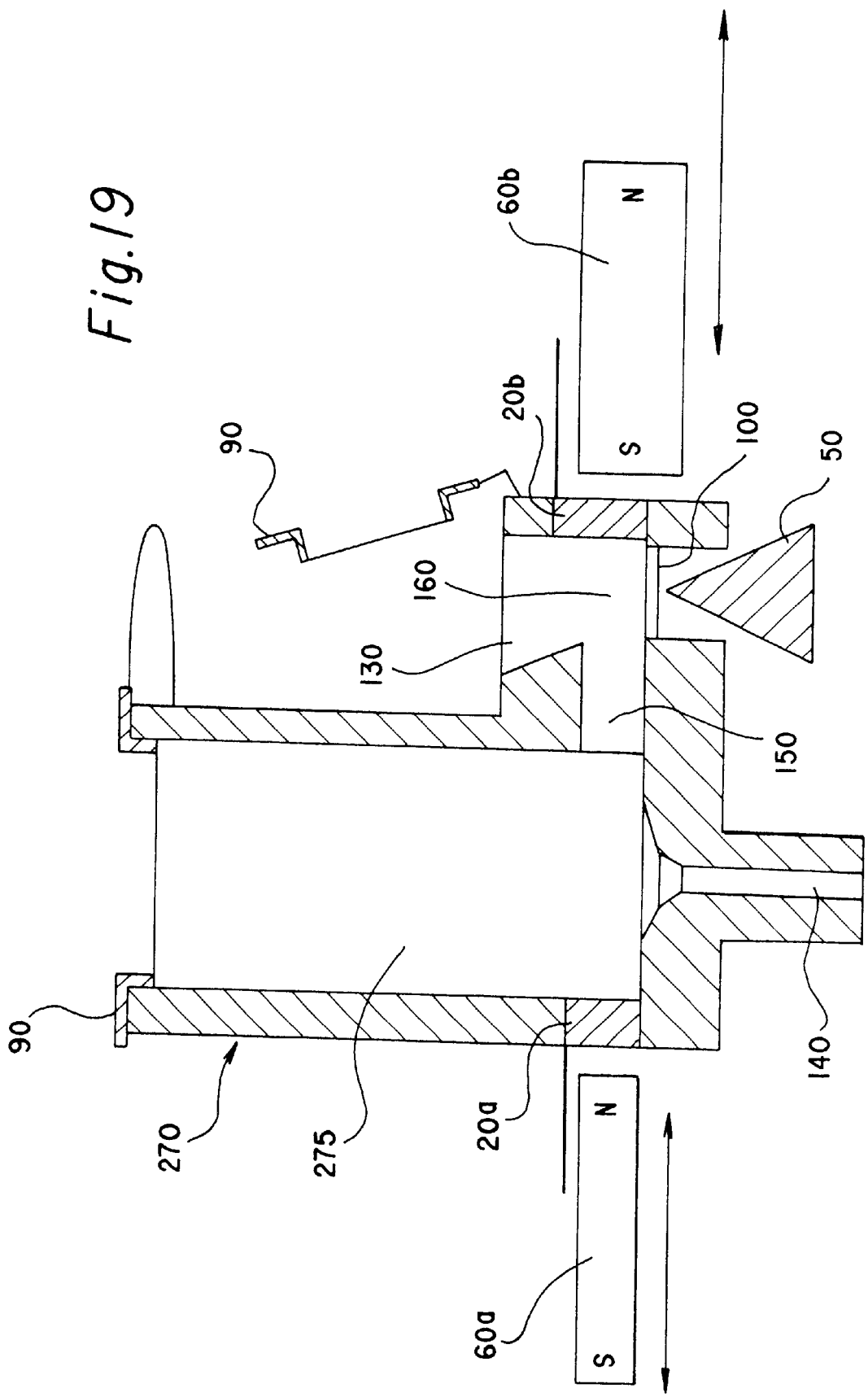

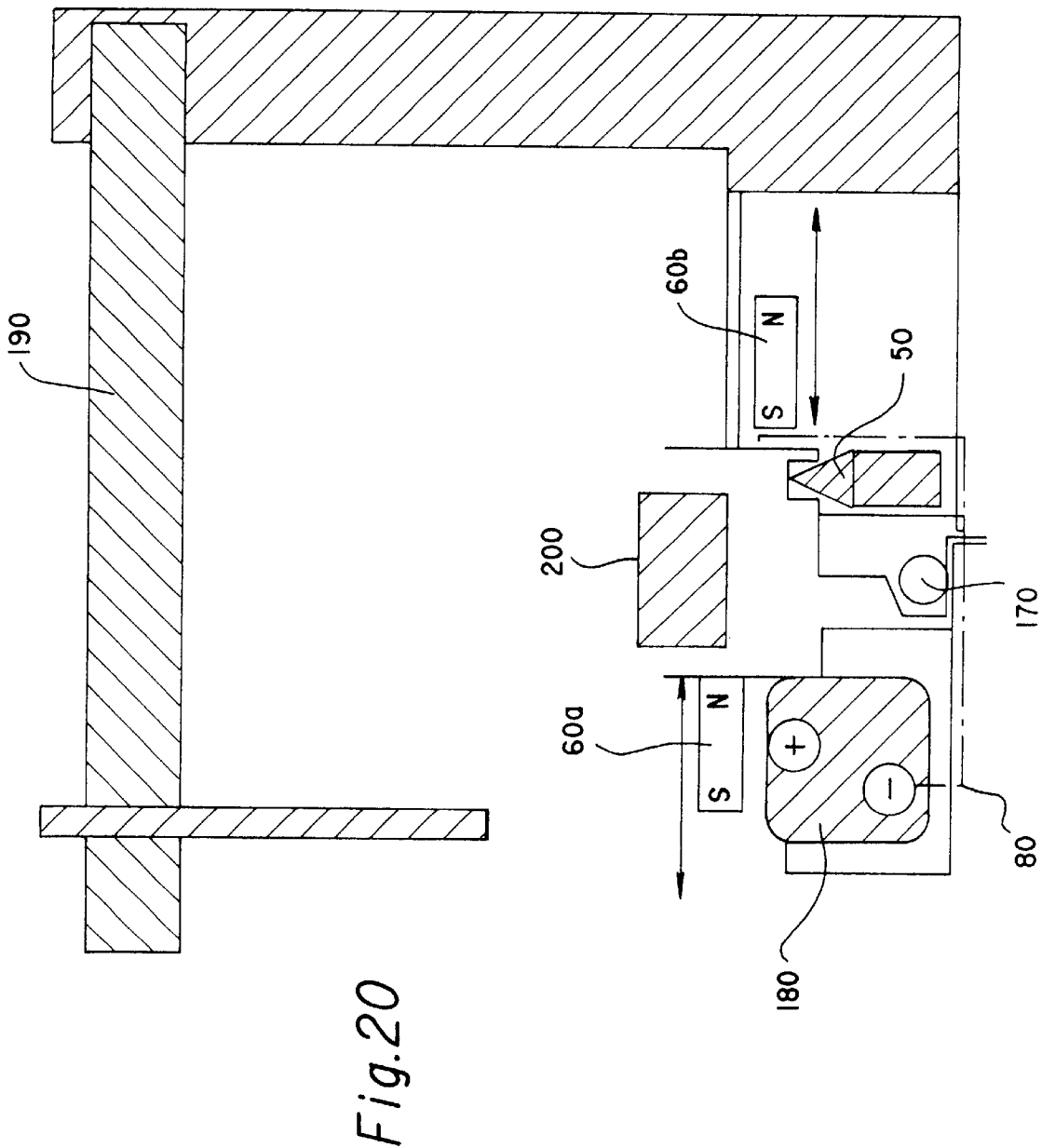

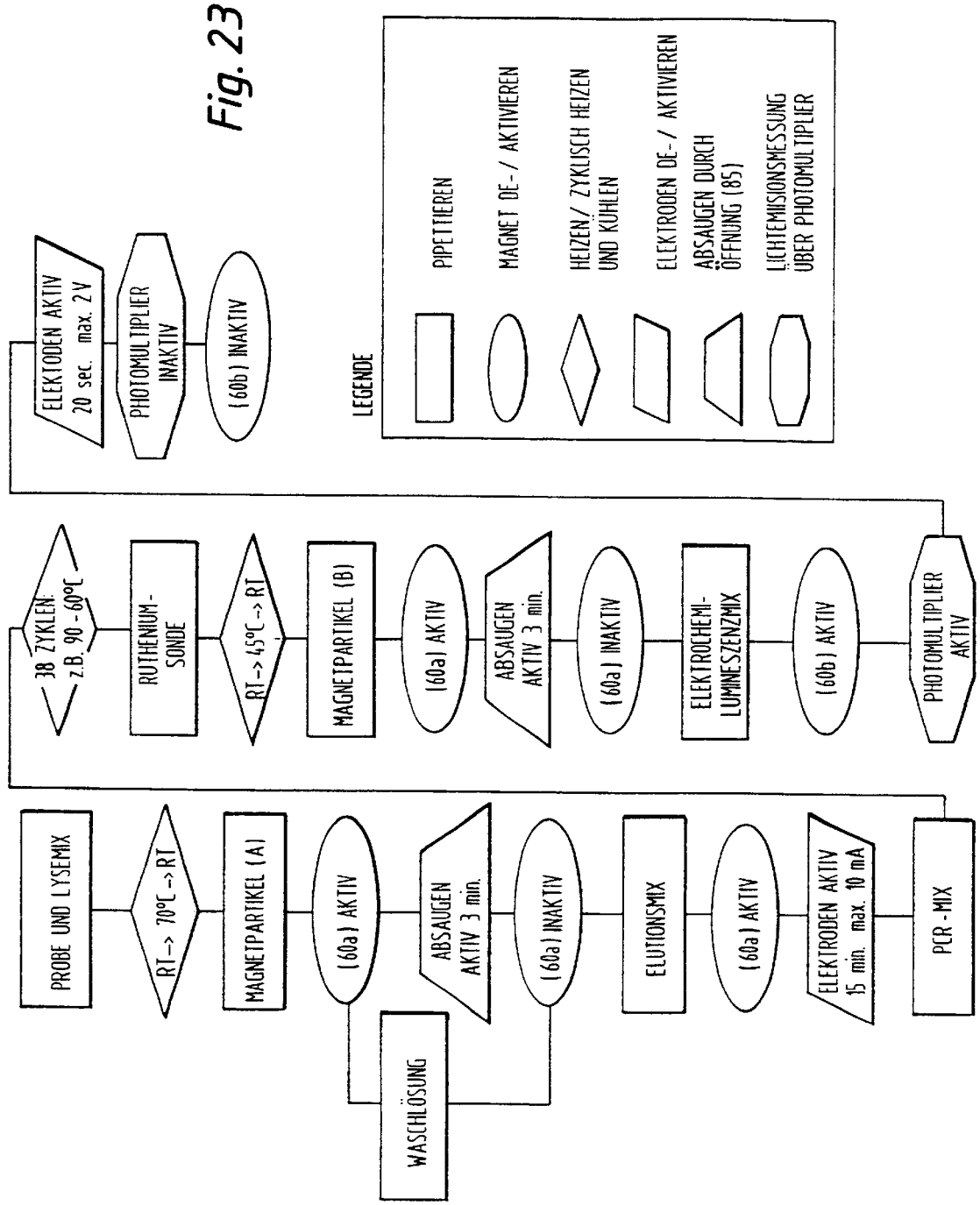

APPARATUS AND METHOD FOR ISOLATING AND/OR ANALYZING CHARGED MOLECULES

The invention relates to apparatus for isolating and/or analyzing electrically charged biomolecules, illustratively to isolate and/or analyze nucleic acids, having a vessel made of a substantially rigid plastic and comprising a collection chamber to receive a reaction mixture of sample and reagents, the collection chamber being externally accessible through an intake aperture of the vessel, and furthermore two electrodes movable into the collection chamber to come into contact with the reaction mixture.

The invention moreover relates to a method for isolating and/or analyzing electrically charged biomolecules, preferably nucleic acids, by adsorbing charged biomolecules contained in a solution to an appropriate adsorbent, by separating the remnant solution and optionally washing the adsorbent, by detaching the biomolecules from the adsorbent and separating the biomolecules, and to using the apparatus of the invention in the method of the invention.

Apparatus of this species are used in biochemical analysis and in the peripheral field of modern pharmaceutical identification of active substances (HST=High Throughput Screening) in the most diverse domains, for instance in nucleic-acid analysis. Illustratively the patent document WO 97/34908, of earlier priority than the present application but published after the priority date of the present application, discloses apparatus of the species wherein the vessel besides a collection chamber also comprises a withdrawal chamber communicating through a transfer duct with the collection chamber. Nucleic acids to be isolated are electrophoretically moved from the collection chamber through the transfer duct into the removal chamber and there are enriched. Moreover the vessel is fitted at its base wall with a pipe stub allowing draining the collection chamber. On the whole the above described vessel is of complex design entailing substantial manufacturing cost. Especially as regards applications in which the apparatus cannot or is not allowed to be used again on given grounds, there is a need for a simpler and more economic problem resolution.

The discussion to follow of further documentation relates to further aspects of such apparatus calling for improvements and the methods of the state of the art used in their operation:

Illustratively further electrophoretic equipment is known using platinum electrodes. Platinum is highly resistant to redox processes and, being an inert electrode material, constitutes a durable solution. However the entailed high material costs, for instance of coated electrodes for single use, are a drawback. Moreover the coating of platinum surfaces is a complex engineering procedure. Plastic electrodes, for instance made of synthetic carbon (BIO Fonum Forschung und Entwicklung, GIT Verlag, $19^{th}$ year, vol 12, 1996, p 584) also are state of the art. However such apparatus are unsuitable for single use because they cannot be made economically, for instance by injection molding. A survey of electrophoretic gel methods is described in "Electrophoresis Theory, Techniques; and Biochemical and Clinical Applications", Ed. A. T. Andrews, ISBN 0-19-854633-5, Clarendon Press, Oxford 1986. Besides normal gel electrophoretic methods, also so-called plotting techniques are described in the above work as well as in a work by Southern (GB 88 10400, 1988), which require corresponding plate electrodes. On economic grounds, platinum electrodes are ruled out entirely. In general V2A steel may also be used.

The patent documents WO 95/12808 and U.S. Pat. No. 5,605,662 describe systems hybridizing nucleic acids and also employing a special electrode configuration. The heart of these documents is micro-apparatus wherein nucleic acids are hybridized. A special stringency check is carried out by electronic interactions with micro-electrodes. The surfaces of these micro-electrodes are made of a material allowing free transport of compensating ions. This apparatus is used to concentrate nucleic acids and to carry out corresponding hybridizations. By appropriately changing the electrode polarity, poorly hybridizing parts of nucleic acid can be removed.

The electrode is coated with an oligonucleotide and can be prepared by microlithography. The following materials are cited for the electrodes: aluminum, gold, silver, tin, copper, platinum, palladium, carbon, semiconductors and combinations thereof. The manufacture of these electrodes or the deposition of the electrodes on certain substances according to the patent documents WO 95/12807 or U.S. Pat. No. 5,605,662 as a rule is implemented by vacuum evaporation or evaporation coating techniques. If appropriately finished, the electrode surface may be coated with biologically active components such as nucleic acids.

The patent document WO 96/15440 describes another procedure requiring electrodes. This so-called electrochemiluminescent method generates a luminescence signal by exciting molecules at the surface of an electrode. Using magnetic fields, illustratively magnetic particles bearing appropriate luminescence labels are transported to the electrode surface. The special embodiment in this document is a reusable in-line cell. This cell comprises a preferably gold electrode. The matching electrode is a corresponding reference electrode. As a rule the matching electrode is a silver/silver-chloride system. All these procedures incur the drawback of using expensive noble metals for the electrode material and consequently are unsuitable for instance for a single-use apparatus.

The patent document WO 97/02487 describes a planar device in the form of a test strip to measure electroluminescence.

A procedure of electro-elution is described in "Methods in Enzymology 65" [pp 371–380, 1980]. Platinum electrodes are used.

A method for coating non-conducting plastic surfaces using avidin or streptavidin is described in the patent documents U.S. Pat. No. 4,656,252 and U.S. Pat. No. 4,478,914 Re. 31,712.

The German patent document A1 195 20 398 describes magnetic particles having a glass surface and which are suitable for isolating nucleic acids and which may be used in apparatus of the present application. A comparable procedure employing porous glass surfaces and covalent bonds is described in U.S. Pat. No. 5,601,979 for nucleic-acid hybridization.

The patent document WO 97/01646 discloses a procedure to electrochemically detect nucleic-acid hybridizations using electrodes consisting of substrates on a surface. According to the patent documents WO 92/20702; WO 92/20703; EP A1 0,618,923 and WO 96/27679, furthermore so-called peptide nucleic acids (PNA) can be advantageously used, besides nucleic acids, in hybridization.

On the other hand it is the objective of the present invention to create apparatus of the initially cited kind which is of simple design and can be manufactured economically.

The invention solves this problem by apparatus of the initially cited kind which furthermore comprises a tube unit made of an electrically non-conducting plastic and dimensioned and/or configured and/or mounted in such manner that at least part of its inside surface may be brought into contact with the reaction mixture contained in the collection chamber whereas the tube unit and one of the electrodes are designed in such manner that this electrode can be brought into contact, inside the tube unit, with the reaction mixture. Because the invention provides the tube unit, the design comprising a vessel with a separately formed removal chamber can be dropped and as a result the vessel is constructed in commensurately simple manner and manufactured correspondingly more economically. In the invention, the removal chamber is present inside the tube unit and as a result this tube unit, being a simple component, contributes only insignificantly to the manufacturing costs of the apparatus as a whole.

The tube unit may be configured inside the vessel in widely different ways:

Illustratively this tube unit may be affixed to one of the electrodes, preferably being attached to it, and it may be inserted into the vessel jointly with said electrode. Furthermore, the second electrode may be affixed to the tube unit, preferably to attach it to this electrode. These embodiment variations are particularly significant regarding apparatus implementing in automated manner the isolation and/or analysis of charged biomolecules while using a robot arm displaced in programmed manner. By means of this robot arm, the electrode(s) and the tube unit may be fetched from corresponding magazines, be attached to each other as desired and be introduced into the vessel.

In addition or alternatively, the tube unit may be affixed to the base of the vessel. To allow exchange of reagents between the vessel and the inside space of the tube unit, the invention proposes that the rube unit be fitted with apertures at its lower end, preferably in the vicinity of the vessel base and/or adjoining to it. Illustratively the tube unit may be fitted with feet standing on the vessel base and separated from each other by slots adjoining the base, the exchange of reagents taking place through these slots between the feet.

Furthermore the tube unit may be affixed to, preferably suspended from, the edge of the intake aperture.

As regards automated implementation of the isolation and/or analysis of the biomolecules, in particular employing a displaceably programmed robot arm, the invention proposes fitting the tube unit with positioning arms to stabilize its position within the vessel. As a result, the tube unit shall reliably always be in the same position relative to the vessel walls and thereby it can be moved accurately into its target position with a programmed displacement of the robot arm, for instance in order to insert the electrode into the inside space of the tube unit.

In one of the simplest embodiment variations, the entire inner space of the tube unit constitutes the electrode chamber. However and equally well, an electrode chamber may be partitioned off in the tube unit's inner space, a communication duct between the electrode chamber and the remnant tube unit inner space being sealed by a semi-permeable membrane. This design prevents the biomolecules displaced to one electrode during electrophoresis, and during isolation of nucleic acid for instance to the anode, from being in contact with this electrode and where they might undergo redox reactions. In order nevertheless to be able to remove in simple manner the nucleic acids enriched in the inner space of the tube unit, the invention proposes fitting the upper end of the tube unit, besides an intake to the electrode chamber, also with an intake to one of the removal chambers near the electrode chamber. In order not to be restricted solely to liquid electrophoretic procedures when isolating and/or analyzing biomolecules, the invention proposes placing a mass of gel, hereafter merely called "gel", in the tube unit of which it occupies the full inside width, whereby gel electrophoretic procedures also may be carried out with the apparatus of the invention.

To effectively isolate biomolecules which on account of the procedural steps discussed above have accumulated at the vessel base, the invention proposes flaring the tube unit from the one electrode toward the vessel base. As a result the "intake region" for electrophoretic isolation of biomolecules can be enlarged in the immediate vicinity of the one electrode.

An illustrative vessel of especially simple design may be implemented in that the vessel have a base free of apertures and a sidewall free of apertures. Such a vessel is manufactured in especially simply and hence economical manner and in conjunction with two electrodes makes it easy to carry out electrophoretic processes even in the absence of a tube unit. Even though the efficiency of electrophoretic isolation of biomolecules is less in the vicinity of an electrode than when a tube unit is used, especially when the biomolecules are to be aspirated from the vicinity of the electrode, on the other hand this lesser efficiency may suffice for some procedures. Accordingly independent protection is claimed for apparatus of which the vessel's base and one sidewall are free of apertures.

If the vessel is made of a thermally deformable plastic, for instance being made by injection-molding, its manufacture shall be especially economical.

The vessel base may comprise at least one zone of lesser base thickness. This feature is especially advantageous for detection, for instance when a detector, preferably a photomultiplier, is mounted within the zone of lesser base thickness.

Just as the vessel, the electrodes too may be made of electrically conducting plastics. On economical grounds it is therefore preferred that the electrodes, or the at least one electrode, shall be manufactured from aplastic containing electrically conducting additives. These additives maybe graphite, iron, silver, gold or other metals and/or their mixtures and/or their alloys.

To achieve good electrical conductivity, the invention proposes that the at least one electrode be of an electrical resistance less than 100 MΩ, preferably less than 1 MΩ. Simple manufacture for instance by injection molding is made possible ifthe electrodes, or the at least one electrode, are made of thermally deformable plastic.

The electrodes may be configured in different ways in the vessel. In particular the electrode mounted in the tube unit may be an element separate from the vessel. Furthermore the electrode may be affixed directly or indirectly to the vessel and/or to the tube unit, preferably it shall be clamped in order that its position be determined to the particular other electrode.

Illustratively, in case enriched biomolecules are removed from the vessel for further analysis, the invention proposes at least one electrode designed as a pipet tip or part of such a tip. The whole pipet tip may be made of an electrically conducting plastic. However and in equally feasible manner, only part of the pipet tip may be made of an electrically conducting plastic, for instance when electrically conducting additives are admixed to a first portion of plastic during injection molding and then a second portion of plastic being processed in pure form. Alternatively and furthermore, a separately manufactured electrode may be mounted in a pipet tip.

The invention proposes to enlarge the area of reaction of the electrode by mounting or forming extensions to the outside of the electrode.

Lastly, at least one electrode may be integral with the vessel wall. Illustratively the entire vessel may be made of an electrically conducting plastic whereby this entire vessel shall constitute the electrode. However it is equally feasible to admix electrically conducting additives to spatially limited segments of the plastic during vessel manufacture, as a result of which for instance the cathode is formed on one side of the vessel and an anode on the other. This design is especially significant for an apparatus without a tube unit and of which the vessel's base and sidewall are free from apertures.

In order to reliably preclude electrical shorts in operation, the invention proposes a spacer preventing bodily contact between the electrodes. To achieve as simple as possible a removal of enriched biomolecules, this spacer may be tubular, preferably to match the outer geometry of a pipet tip.

In order to implement the insertion of electrodes and spacer into the vessel in the fewest possible steps, the spacer and at least one electrode may be made into one unit. Moreover the spacer may be designed to be a pipet tip.

As already intimated several times in the above discussion, the electrodes may be connected to an external power supply.

In one preferred embodiment of the invention, at least one of the electrodes and/or the semi-permeable membrane is fitted with a coating. Such a coating makes it possible to bind the biomolecules to be isolated and/or analyzed to the electrode or to the semi-permeable membrane. The electric field enhances the rate of binding and the physical approach of the biomolecules to the electrode and/or the semi-permeable membrane. Preferably however the binding shall take place at the semi-permeable membrane because thereby fewer degradations will be applied to the biomolecules on account of the redox reactions or the like taking place in the vicinity of the electrode or on account of heat dissipation.

Because of this binding by means of the coating, the biomolecules on one hand are easily isolated by removing the electrode or the membrane from the apparatus and on the other hand detection of the bound biomolecules may be advantageously carried out in known manner.

If such a biomolecules is a protein, then illustratively a labeled antibody against this protein may be added and the binding of the antibody to the protein can be determined by the label and thereby the presence of the protein in qualitative and/or quantitative manner. Illustratively detection also may be by means of electrochemiluminescence as basically described for instance in the patent document WO96/15440.

On the other hand the biomolecules also may be a nucleic acid which the expert again may detect by known methods.

The coating of the electrode and/or the membrane preferably shall be multi-layer. Preferably the coating shall comprise one or more biological polymers. Suitable biological polymers in particular are molecules easily deposited on the surfaces of electrodes or membranes and which furthermore are able to impart direct or indirect, specific or non-specific binding of biomolecules. Such biological polymers are known per se. Preferred polymers include proteins, and bovine serum albumin (BSA) again is a preferred protein. BSA in general enables non-specific binding though upon pertinent pretreatment it may also be able to impart specific binding.

Such pretreatment may for instance thermal. Such pretreated BSA then can be used as a binding allowing avidin or streptavidin to form a further layer of biological polymers.

In a further prefeed embodiment of the invention, the biological polymer is a binding-specific protein. Such binding-specific proteins are known to the expert and they are preferably in the widest sense partners of specific binding pairs. The presence of a partner of a specific binding pair at least in one layer of the coating is another preferred embodiment of the invention. Specific binding pairs also are generally known, for instance being pairs of ligand and receptor, this being a very broad definition which also may include the following binding pairs such as antigen/antibody or antibody fragment, hapten/antibody or antibody fragment, and biotin/(strept)-avidin.

When a partner of a specific binding pair is integrated in the coating of the electrode or the membrane of the invention, the biomolecules to be isolated and/or analyzed either is conjugate with the other partner of the binding pair or else the biomolecules itself is the other partner.

An especially preferred multilayer coating is composed of pretreated BSA to which is bound steptavidin. Any molecule conjugate with biotin can be bound to this coating.

On the other hand in a highly preferred manner of the invention, regarding the isolation and/or analysis of proteins, their receptors or antibodies specifically directed at the protein shall be integrated into the coating.

In a further preferred embodiment, the biological polymer present in the coating is in the form of at least one nucleic acid or one oligonucleotide. These molecules too can be bound directly by adsorption to the electrode or the membrane or else, by means of a specific binding pair, optionally still in combination with further coating layers such as BSA.

By means of a nucleic acid or a polynucleotide or oligonucleotide present in the coating, it is possible to bind by hybridization nucleic acids such as DNA or RNA to be isolated or analyzed.

Furthermore other coatings able to bind the nucleic acids are appropriate within the scope of the present invention. Preferably such include peptide nucleic acids which were cited already above in relation to the Patent documents WO92/20702; WO92/20703; EP A1 0,618,923 and WO96/27679. The PNAs described therein in principle can also be used within the scope of the present invention.

Aside from the above discussed, preferred embodiments of the invention, or in combination with them, the coating may preferably also contain reactive linker molecules in at least one layer. Such linker molecules allow coupling biological polymers using covalent bonds to the electrode or membrane. Optionally further layers of preferably biological polymers may adjoin the biological polymers coupled by linker molecules.

In a further development of the invention, appropriate adsorbents are present or can be introduced in the vessel in order to separate the biomolecules from other substances. Illustratively the adsorbents may be silica gel and/or agarose gel and/or polyacrylamide gel and/or ion-exchange substances and/or fiberglass and/or glass particles and magnetic particles preferably enclosed in glass with special nonwovens adsorbent properties.

High efficiency of isolation of biomolecules by adsorption at an appropriate adsorbent can be achieved provided this adsorbent be distributed as uniformly as possible in the vessel. When the biomolecules are removed from the vessel, or when they are analyzed within it, on the other hand, they are preferably concentrated at a predetermined site. Accordingly the invention proposes in a further development fitting the vessel with a magnetic field source which can be switched between an active state wherein it exerts an attractive force on magnetic particles whhin the vessel and an inactive state wherein it exerts no force, or only an insignificant one, on these particles. Illustratively the magnetic field source may be a permanent magnet and/or a body of magnetizable material. However the source also may be in the form of an electromagnet switched between the active an inactive states. In both cases, when the magnetic field source is a permanent magnet and when it is an electromagnet, the switching between the active and inactive states also may be implemented by the source being moved between a near-vessel position corresponding to the active state and a position remote from the vessel corresponding to the inactive state, for instance by the source being tipped or shifted away.

If the apparatus of the invention is fitted with a robot arm displaceable in programmed manner, for instance in the form of an arm of a pipetting robot then this robot and said magnetic field source may be matched to each other in such manner that the switching between the active and inactive states is implemented by the pipetting robot alone. Illustratively the robot arm can implement the switching between the said active and inactive states by resting against a tipping switch, a setting lever or a tipping lever.

To assure in simple manner the assembly of the apparatus of the invention in its manifold embodiment variations, the invention proposes that the pipetting robot besides the pipetting plunger also comprise a gripper.

A further concept of the invention relates to a combination structure of apparatus of the invention whereby the apparatus anodes are connected to one another and the cathodes of the apparatus are also connected to each other. Furthermore the tube units of the apparatus of the invention can be combined into one combination structure, whereby all vessels can be fitted with an associated tube unit by a single motion of the robot arm. Such a combination structure is especially suitable to carry out series tests for instance of a plurality of nucleic acid samples. In such a combination structure, the vessels may be combined into one microtitration plate.

Moreover the invention relates to a basic unit comprising at least one seat for an apparatus of the invention and/or a combination structure of apparatus of the invention. This basic unit may comprise prefabricated receptacles for at least one magnetic body or electromagnet. However it may also be already fitted fully with at least one magnetic field source. Moreover this basic unit may be fitted with at least one electric feed conductor to make contact with at least one electrode. The plurality of applications may be raised further in that the at least one seat shall be heatable and/or coolable.

Another objective of the present invention is a method of the initially cited kind. The method of the invention is used to isolate and/or analyze charged biomolecules by adsorbing charged biomolecules in solution at a suitable adsorbent, by detaching the remaining solution and optionally washing the adsorbent, separating the biomolecules from the adsorbent and separating the biomolecules, said method being carried out in an apparatus of the invention or in a combination structure of such apparatus of the invention, and at least the detachment of the biomolecules from the adsorbent being implemented by electroelution.

The scope of the present invention also includes methods wherein the adsorbent already loaded with charged biomolecules is directly inserted into an apparatus of the invention, as a result of which therefore the procedural steps of adsorption at an adsorbent and separation of the remaining solution and optionally washing are eliminated. Because the present invention foremost applies to the elution and separation of the biomolecules, the insertion of an adsorbent loaded with biomolecules also must be construed as being part of the present invention.

Within the scope of the present invention, "electroelution" means the detachment of the biomolecules from the adsorbent by an applied electric field generated between the electrodes in the apparatus. The charged biomolecules migrate in the electric field according to the electric charge and may be accumulated in the vicinity of the oppositely polarized electrode. Biomolecules may be charged both positively and negatively. Nucleic acids are charged negatively and will migrate in the electric field to the anode. Depending on their amino-acid composition, proteins may have a net excess positive or negative charge. Depending on the biomolecules to be analyzed and/or isolated, the electrodes of the apparatus of the invention may be polarized in such manner that the isolation and/or analysis can be carried out advantageously.

The adsorbent by means of which the charged biomolecules are separated from other substances present in the solution preferably is selected from a gel, an ion-exchanger substance, fiberglass nonwovens and glass particles, in particular magnetic particles enclosed in glass. The gels may be generally known separation gels such as agarose or polyacrylic amide gels as well as silica gels or the like. Preferably, when using glass particles, the glass surface shall appropriately be pretreated or modified to bind biomolecules. Such glass particles, mostly called "beads", are known to the expert and are made by many enterprises.

Furthermore the apparatus of the invention may be used to elute charged biomolecules out of a gel by being configured jointly with electrophoretic buffers between two electrodes of the invention in a reaction vessel, the electrophoretic flow resulting in release from the gel.

Following binding the charged biomolecules to the adsorbent, the ion strength of the solution where necessary may be matched to the adsorbent in the process of electroelution. This matching may be implemented either by salting the present solution, for instance the last wash solution, or preferably by adding an electroelution buffer of appropriate ionic strength.

Preferably the biomolecules shall be separated by means of the electric field in the vicinity of the electrode polarized oppositely to the molecules.

Due to the application of an electric field, the biomolecules migrate out of the adsorbent, i.e. they are detached, and then move toward the oppositely polarized electrode.

Surprisingly and in a preferred embodiment, the detachment is substantially improved by raising the temperature to 30 to 100° C., preferably 55 to 80° C.

In another preferred embodiment of the invention, the starting point is not a solution containing charged biomolecules in their free form, but instead a solution comprising cells is used, preferably intact cells, containing the biomolecules. These cells are bound to an adsorbent such as magnetic glass particles. After the cells have been adsorbed, they are lysed and subsequently released, charged biomolecules will be concentrated by means of an electric field in the vicinity of the oppositely polarized electrode. Molecules to be isolated from the cells are, in the invention, especially nucleic acids.

Preferably again, the biomolecules released from the cells shall be once more subjected to separation from other, by released molecules being bound once more to an adsorbent, for the purpose of achieving better isolation and analysis. The renewed adsorption may be carried out using the same but also different adsorbents, depending on the adsorbent specificity.

Illustratively, in order to isolate biomolecules only from cells of a specific kind, an adsorbent may be used which comprises receptors for surface antigens of specific cells. The expert is conversant with feasible applications and variations regarding the biomolecules to be isolated, and such applications and variations are easily implemented by means of the remaining disclosure of the present invention.

Moreover the method of the invention remains unchanged, that is, elution and separation are carried out as already described above for the previous configurations.

In a further preferred embodiment of the invention, glass-enclosed magnetic particles are used as adsorbents and, during elution of the biomolecules, are kept spatially separate from the biomolecules by means of the magnetic field source. In particular this feature is implemented in that following biomolecular adsorption, the magnetic field source and the electrodes simultaneously act in spatially opposite manner on the magnetic particles and the biomolecules in order to carry out elution and separation. In this process the biomolecules are concentrated in the vicinity of the oppositely polarized electrode whereas the magnetic particles are preferentially collected by the magnetic field source at the most remote possible distance. In this manner it is possible to avert degradation caused by the magnetic particles when removing or analyzing the biomolecules.

In one implementation of the invention, namely when isolating the biomolecules, they will be removed from the vicinity of the oppositely polarized electrode, and preferably they will be pipetted off. The solution of the elution buffer then contains concentrated biomolecules. If apparatus of the invention is used, wherein one of the electrodes or the semi-permeable membrane is coated to bind the molecules, it is then possible to directly remove the electrode and/or the semi-permeable membrane with the biomolecules bound thereto. In a preferred implementation of the invention, the electrode per se is a pipet tip and any not yet fully bound biomolecules may then also be pipetted off at the same time.

When the charged biomolecules to be isolated or analyzed are nucleic acids, the binding by the method of the invention preferably takes place at a coating containing a complementary nucleic acid of the electrode and/or semi-permeable membrane, by means of hybridization.

In a further implementation of the method of the invention, the charged biomolecules not only are isolated, but they are also analyzed in the very apparatus of the invention. On one hand this analysis can be carried out by labeling the biomolecules and detecting the label in known manner, optionally using chemiluminescent methods such as cited above and detection being by a photomultiplier. Corresponding publications about similarly applicable procedures already were cited above.

On the other hand, a problem may arise precisely when analyzing nucleic acids in that often they are present only in minute quantities. The apparatus of the invention offers the specific advantage that the isolation of nucleic acids and further reactions, in this instance preferably polymerase chain reactions (PCR), can take place in the very same apparatus. In an especially preferred implementation of the method of the invention, following separation of the nucleic acids, therefore all the reagents needed for PCR are added and the amplification is carried out in manner known per se. In an especially preferred mode, the apparatus of the invention are used in a basic unit fitted with heatable or refrigeratable receptacles. In this manner the heating and cooling phases taking place during PCR can be controlled in especially advantageous manner. However and in equally feasible manner, individual apparatus may be used and these may be temperature-regulated in appropriate manner.

Following PCR, the amplified nucleic acids preferably are concentrated again with the help of the electric field and/or are bound to the electrode and/or semi-permeable membrane. Conceivably as well, again a new tube unit may be inserted after amplification into the apparatus of the invention containing a gel by means of which it is possible to resolve the obtained nucleic acid in size by the electric field causing migration through the gel.

A further application of the invention of the above described apparatus relates to fully automated electrophoresis which may be used foremost in the general area of active ingredient identification (High Throughput Screening). Embodiments of the apparatus of the invention filled with gel-like substance are especially significant. Such apparatus may be displaced by the gripper system of an xyz robot. Thereupon, using the electrode system of the invention, electrophoresis may be carried out and subsequently a corresponding detection to investigate the substance mixture separated according to molecular weight. Such detection for instance may be carried out by dyeing the bands in a dyeing bath or using a corresponding optical detection unit such as a fluorometer. In this procedure the corresponding modules may be appropriately displaced by the gripper system over the operational surface.

In a variation of the method of the invention, therefore, the procedure consists in isolating and/or analyzing biomolecules by depositing a sample containing them on a separation gel and by electrophoretically separating the biomolecules on the basis of different molecular weights, said procedure being characterized in that it is carried out in apparatus of the invention or a combination structure of such apparaus. The molecules separated by electrophoresis remain in single bands in the separation gel and can be detected already in the apparatus of the invention or after removing all or part of the gel from the apparatus.

Another objective of the present invention is to use an apparatus of the invention, a combination structure of apparatus or an apparatus combined with a basic unit to implement the method of the invention.

The invention is elucidated below by illustrative embodiments shown in the attached drawings.

FIG. 1 is a perspective elevation of the first embodiment of the apparatus of the invention with a separate cathode;

FIG. 2 is a view similar to FIG. 1 of a modified embodiment comprising a cathode in the form of an electrically conducting reaction vessel;

FIG. 13 is a sectional side view of a further modified embodiment;

FIG. 13a is a simplified schematic top view of the embodiment of FIG. 13;

FIG. 16 is a top view of a combination structure of apparatus of the invention;

FIG. 16a is a perspective of the combination structure of FIG. 16;

FIGS. 17–19 are sectional side views of further apparatus elucidating various detection modes;

FIG. 20 is a schematic side view of a system to isolate nucleic acids, to amplify and to detect by electrochemiluminescence;

FIG. 23 is a functional diagram to control fall analysis of nucleic acids using magnetic glass particles.

Figure 1A:
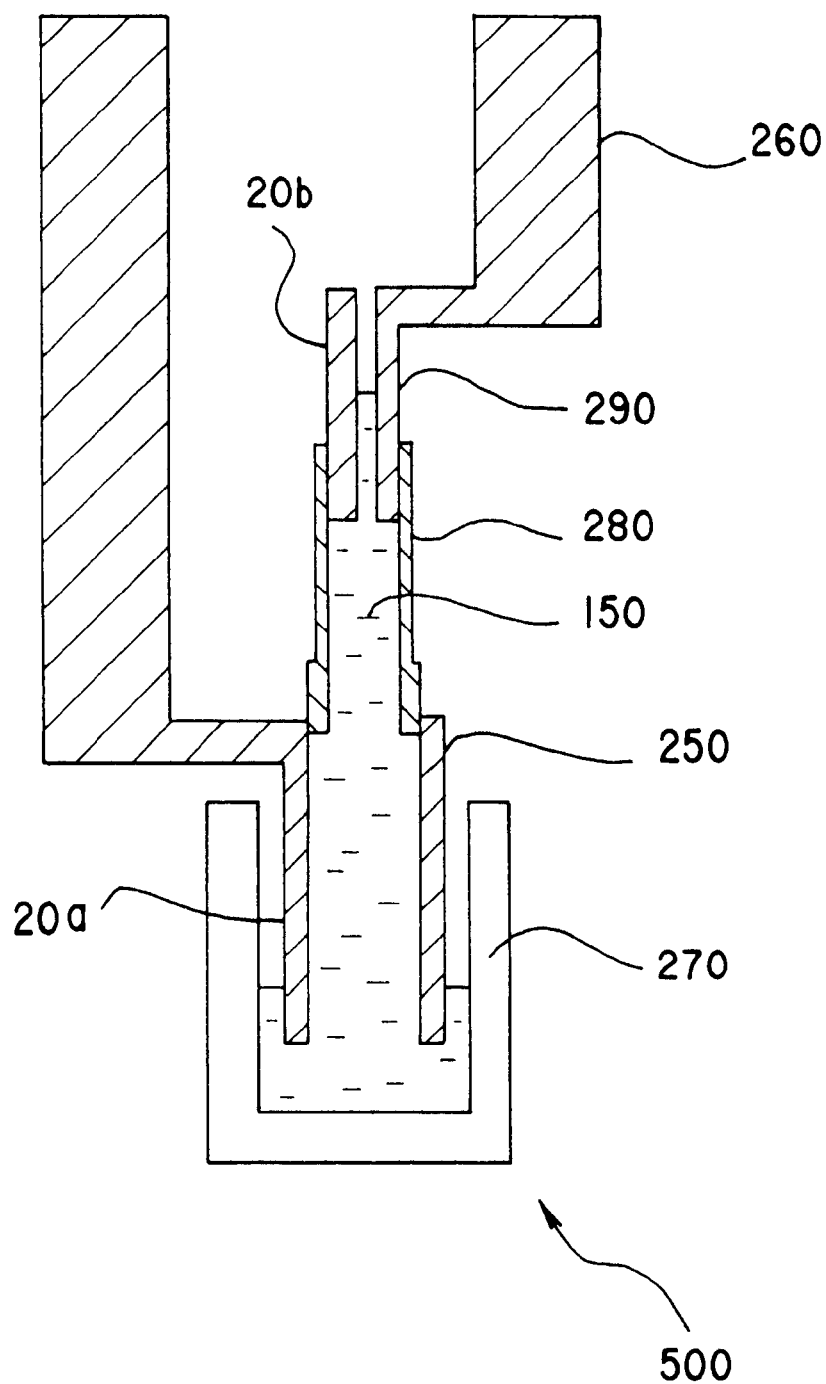
FIG. 1a is a simplified schematic side view (not to scale) of an embodiment of FIG. 1.
Figure 1B:
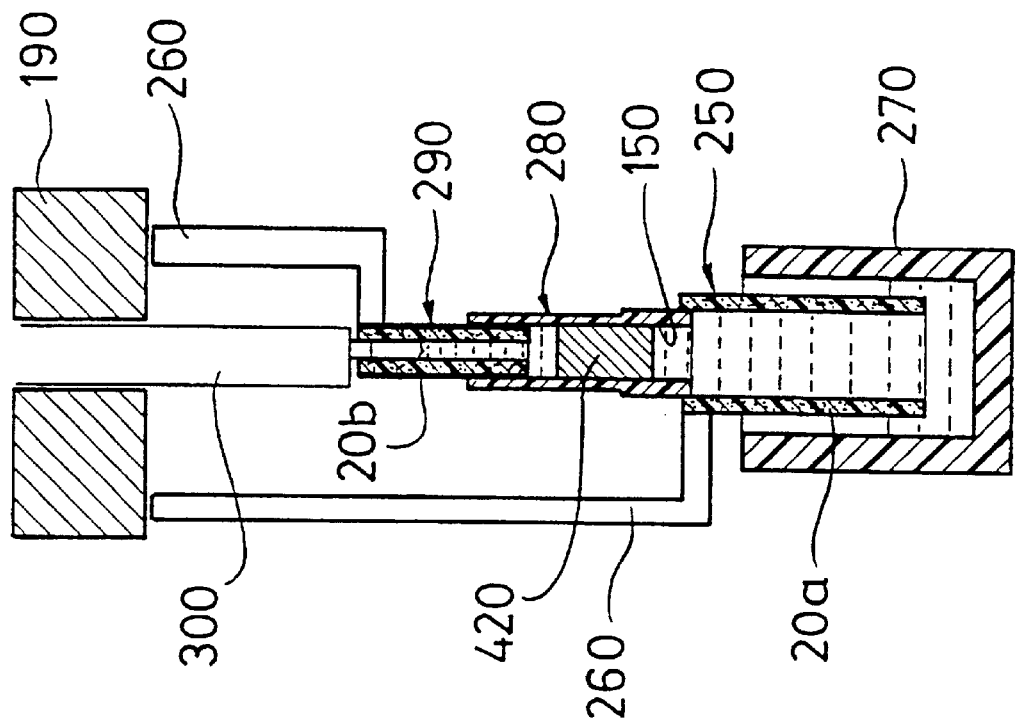
FIG. 1b is an elevation similar to FIG. 1a additionally showing the pipetting unit of a pipetting robot.

An apparatus of the invention to isolate and/or analyze nucleic acids is denoted in overall manner in FIG. 1 by 500. This apparatus comprises a plastic reaction vessel 270, a cathode 20a, an anode 20b and a spacer 280. Both the cathode 20a and the anode 20b are made of a plastic containing electrically conducting additives such as graphite. Moreover the anode 20b is a tube 290 which as shown in FIG. 1b can be attached in the form of a pipet tip 290 onto the piston/cylinder unit 300 of a pipetting robot 190. A voltage may be applied by means of the electric feed conductors 260 to the electrodes 20a and 20b.

The tubular spacer 280 is made of an electrically non-conducting plastic. The inside diameter of this tubular element 280 is so matched to the outside diameter of the anode 20b that these two components can be telescoped into one another in preferably sealing manner after they have been removed form their particular magazines, for instance on account of a corresponding, programmed displacement of the pipetting robot 190. The same relation applies to the outside diameter of the tubular element 280 and the inside diameter of the cathode element 250. Again the outside diameter of the cathode element 250 is selected in such manner that said element can be inserted from above (at 272) into the receiving chamber 275 of the reaction vessel 270 without contact being made (FIG. 1a).

In the embodiment of FIGS. 1, 1a and 1b, the tubular element 280 assumes a number of functions. On one hand it acts as a spacer preventing bodily contact between the electrodes 20a and 20b and hence a short. Furthermore its inner space constitutes a trrnsfer duct 150 allowing the nucleic acids to migrate into the pipet tip/anode 290 on account of their negative charge and the voltage applied across the cathode 20a and the anode 20b.

Moreover, in order to assure the tubular elements 250, 280 and 290 are seated in clamped manner, these elements when nesting in each other also may be fitted each with snugly fitting cone. Such a design also provides the required sealing of the assembly at the nesting sites.

Illustratively the procedure to isolate nucleic acids is as follows: First the pipetting robot 190 removes a pipet tip 290 constituting the anode 20b from a pipet-tip magazine and, in a corresponding further magazine, connects it to the non-conductive tube element 280 by means of a suitable press-fit. Lastly the cathode 20a is added in a further connecting step. Before assembling the unit of anode-spacer-cathodes, the reaction vessel 270 had been filled by the pipetting robot 190 with sample and reagents. Now the unit of anodes/spacerlcathode together with the cathode 20a/250 and optionally also with the spacer 280 is dipped into said reaction mixture. By driving the cylinder-piston unit 300, the reaction miuuure is sucked out of the reaction vessel as far as into the pipet tip 290, care being taken however that the cylinder-piston unit 300 shall not come into contact with the reaction mixture. If now a voltage is applied across the cathode 20a and the anode 20b, the nucleic acids contained in the reagents will migrate to the anode 20b, that is into the pipet tip 290. Upon nucleic-acid enrichment in the pipet tip 290, these reagents contained in the transfer duct 150 of the spacer 280 and of the cathode 250 following controlled expulsion can be isolated and accordingly be prepared for transfer into an analyzer.

To assure that the nucleic acids will accumulate solely in the inner space of the pipet tip 290, the reaction mixture must be present exclusively in the inner space of the pipet tip 290 when the voltage is applied across the cathode 20a/250 and the anode 20b/290. Accordingly at least the pipet tip 290 may not be dipped below the level of the reagents in the vessel 270. Because the reaction mixture was aspirated as far as the anode 20b/290 before the electrophoretic procedure began, the spacer 280 need not necessarily dip by its outside surface into the reaction mixture.

Basically the apparatus 500 of the invention also allows canying out gel electrophoresis. For that purpose an electrically conducting gel 420 may be present in the inner space of the non-conducting tube element 280, that is in the transfer duct 150, said gel occupying the whole inside width of said duct (FIG. 1b). Illustrative, appropriate gels include commonplace agarose gel or a polyacrylic amide gel for instance in preparatory and/or analytical gel electrophoresis.

In the invention filiermore, the apparatus 500 also may be used for electroelution, for instance an adsorbent loaded with nucleic acid being mounted in the reaction vessel 270. By coating with a corresponding electrophoresis buffer and filling the full unit of cathode/spacer/anode with electrophoresis buffer, the nucleic acid can be transferred from the adsorbent into the pipet tip 290 after a voltage has been applied across the electrical feed conductors 260.

FIG. 2 shows an embodiment variation wherein the reaction vessel 270 is made of an electrically conductive plastic, whereby it simultaneously assumes the function of the cathode 20a. A sub-assembly of an anode 20b constituting the pipet tip 290 and a tube element 280 made of a non-conducting plastic is inserted into this reaction vessel 270. As was the case for the embodiment of FIGS. 1, 1a and 1b, care must be paid here too that following aspiration of the reaction mixture out of the reaction vessel 270 this reaction mixture only has gone as far as in front of the inner space of the pipet tip 290 prior to applying the voltage across the terminals 260 at the pipet tip 290 in order to prevent nucleic-acid enrichment at the outside of the anode 20b/290. In this instance too a gel with which to cany out gel electrophoresis may be present in the non-conductive tube element 280.

Figure 3:
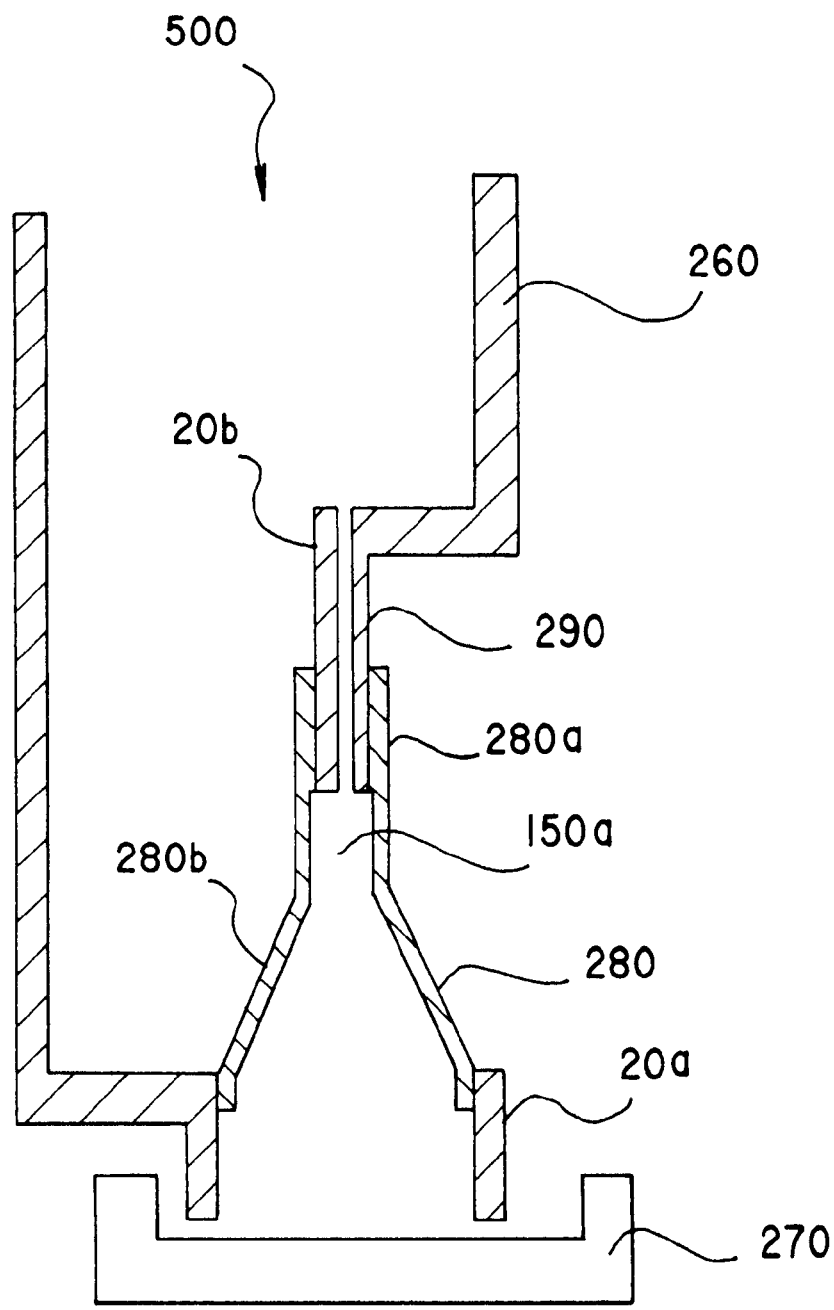
FIG. 3 is a view similar to FIG. 1a of a further modified embodiment.

FIG. 3 shows another embodiment comprising a specially configured, electrically non-conducting tube element 280. This tube element 280 comprises an upper, essentially tubular, cylindrical segment 280a adjacent to the anode 20b and an adjoining lower segment 280b flaring conically toward the cathode 20a. This design makes possible especially effective concentration of nucleic acids that illustratively initially are in the vicinity of the base of the reaction vessel 270, on account of a funnel effect, in a tiny volume 150a underneath the pipet-tip/anode 290. This space can be evacuated upward by means of the pipet tip 290. Obviously gel electrophoresis can also be carried out in this design.

Figure 4:
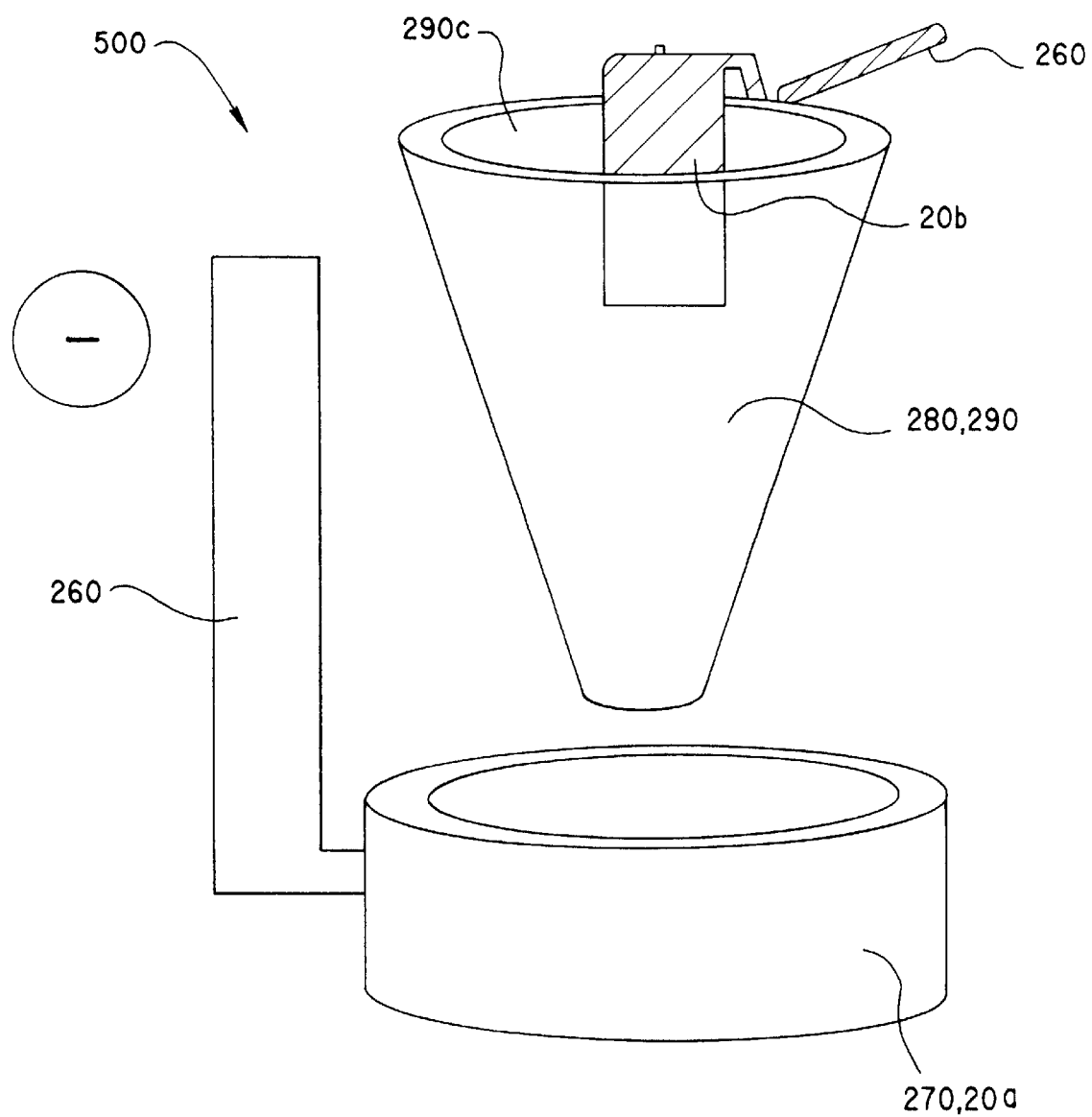
FIGS. 4–6 are perspectives of modified embodiments.

As regards the embodiment shown in FIG. 4, the electrically non-conducting spacer 280 is designed as the pipet tip 290. A specially configured anode 20b is inserted at the upper end of this pipet tip 290 into its inner space 290c. Even though in this embodiment the reaction vessel 270 is made of an electrically conducting plastic and therefore simultaneously acts as the cathode 20a, it is understood that the pipet tip 290 forming the spacer 280 can also be used in a reaction vessel 270 housing a separately constituted cathode 20a. Upon carrying out electrophoresis, there is enrichment in nucleic acids in the pipet tip 290 of the embodiment of FIG. 4.

Figure 5:
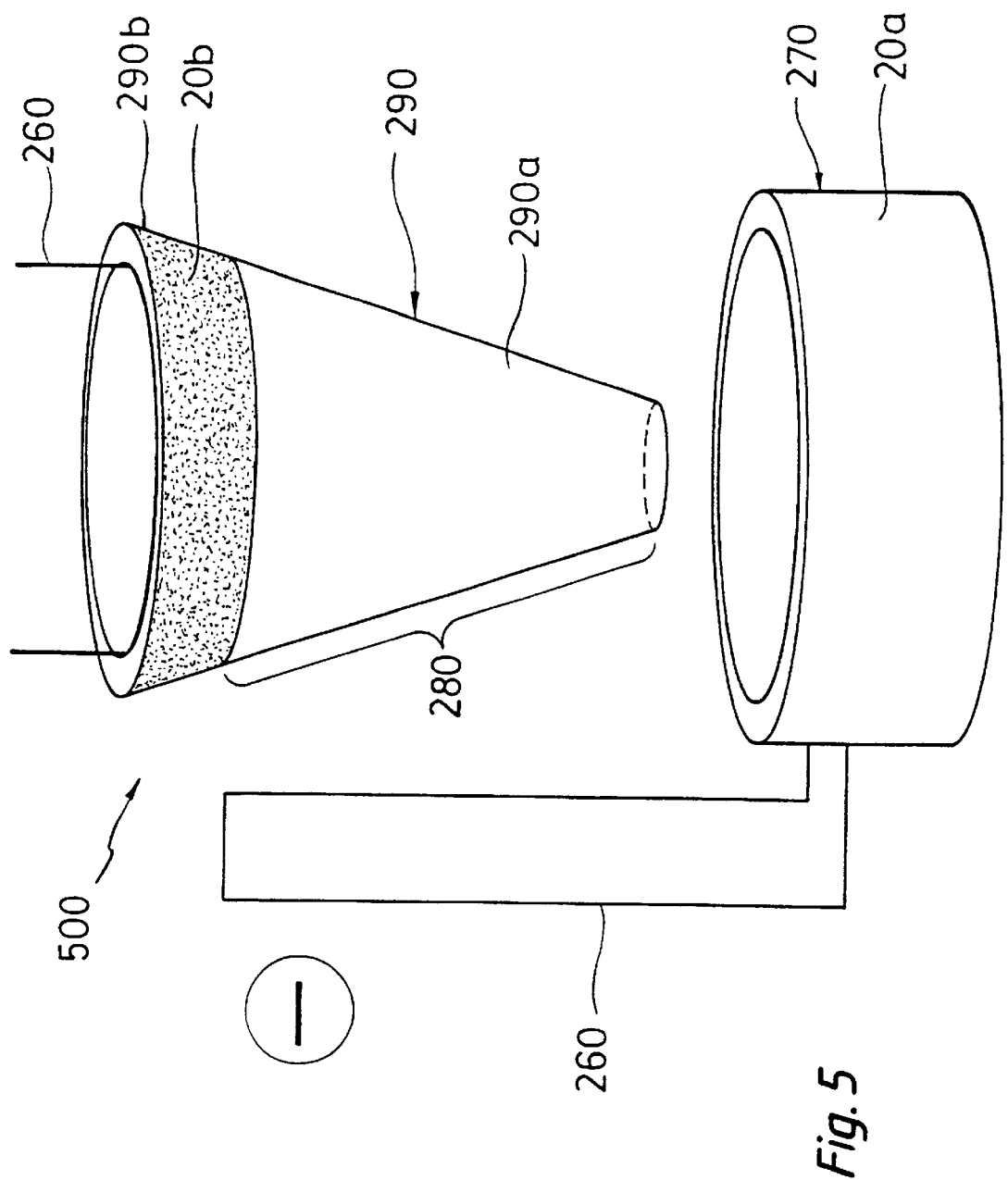

The embodiment of FIG. 5 differs from that of FIG. 4 only by the designs of the pipet tip and the cathode. As shown in FIG. 5, the pipet tip 290 comprises a lower segment 290a, made of a non-conducting plastic and constituting the spacer 280 and it further comprises an upper segment 290b integral with the segment 290a and of which the plastic however includes electrically conducting additives in order that said segment 290b constitute the anode 20b. Otherwise the embodiment of FIG. 5 corresponds to that of FIG. 4.

Figure 6:
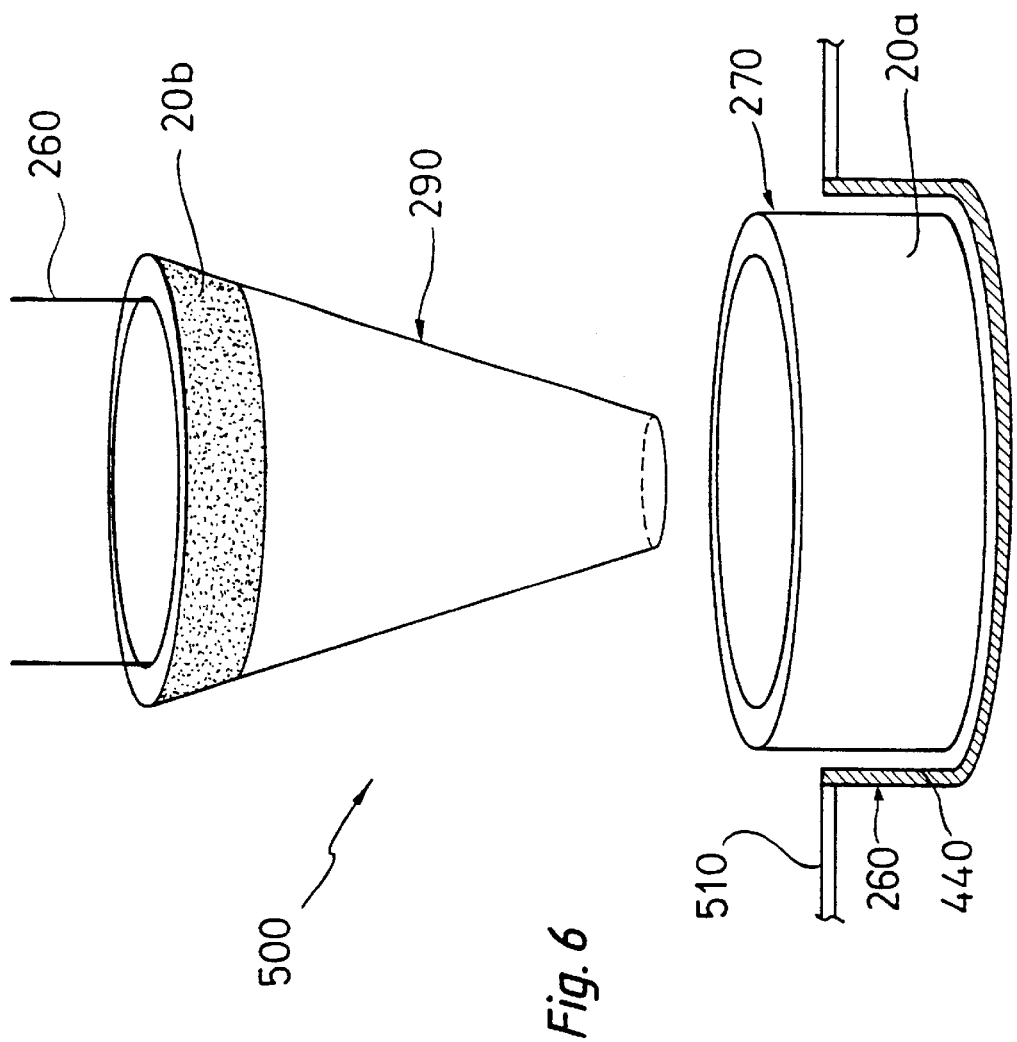

FIG. 6 illustrates an embodiment variant of the electrical terminal 260 of the cathode 20a when latter is constituted by a reaction vessel of electrically conducting plastic. This terminal 260 is formed by a receptacle 440 in a base plate 510 which consists either totally or at least in the region of the receptacle 440 of an electrically conducting material, for instance a metal. The electrical contact between the terminal 260/440 and the cathode 20a is assured by bodily contact when the reaction vessel 270 is moved into the receptacle 440. Making the base plate 510 or the receptacles 440 of metal offers the advantage of better contact and of allowing faster thermal regulation of the reaction vessel 270, the latter feature being especially significant when handling nucleic acids.

Figure 7:
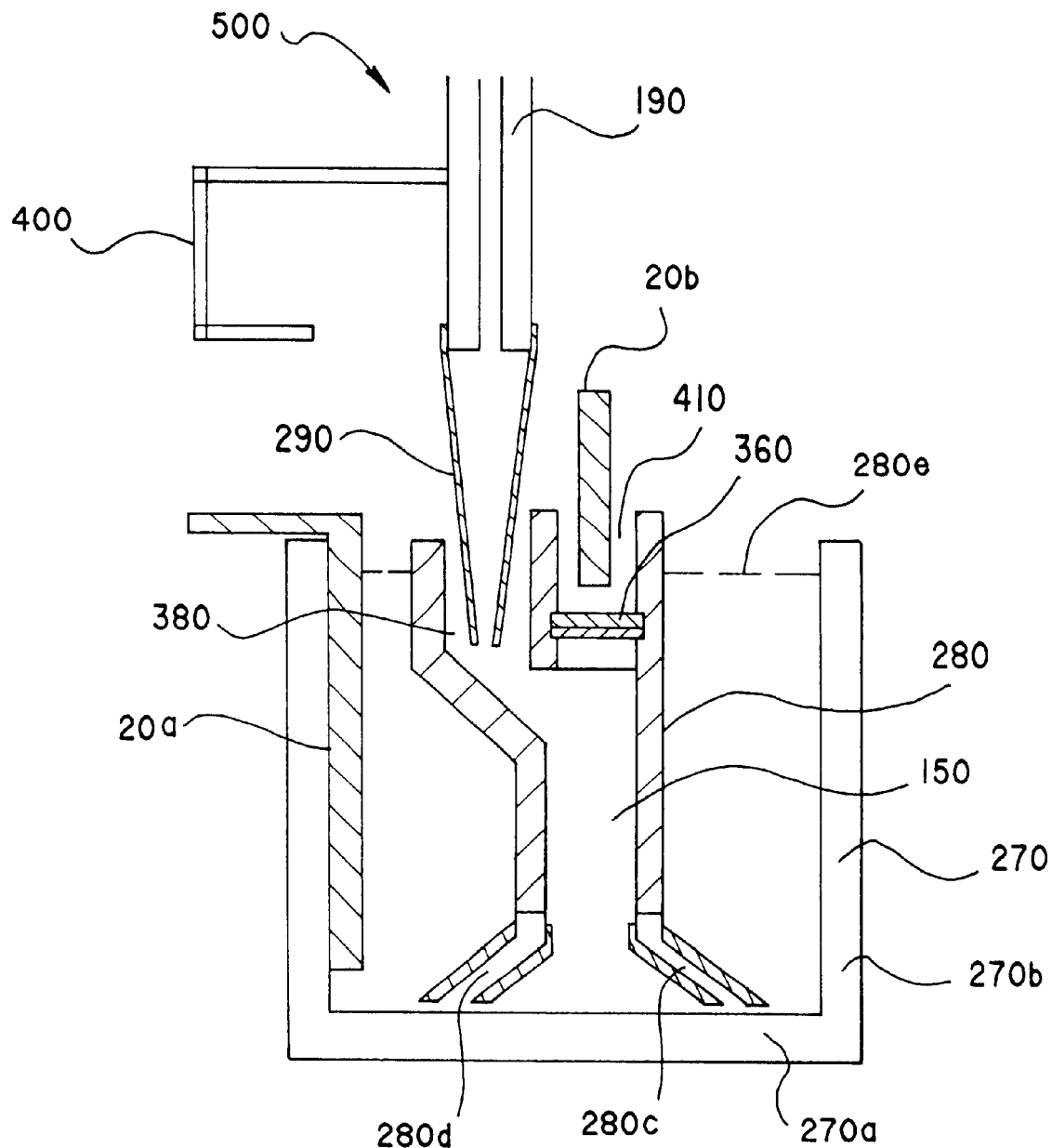
FIGS. 7–11 are sectional side views of further modified embodiments.

FIG. 7 shows another embodiment of the invention. In this embodiment, the spacer 280 stands by feet 280c on the base 270a of the reaction vessel 270. Apertures 280d are present between the feet 280c and allow exchange of reagents between the inner space of the spacer 280 and the reaction vessel 270.

A transfer duct 150 runs in the spacer 280 and above this duct the inner space of the spacer 280 branches out. The linear continuation of the transfer duct 150 is designed as the anode chamber 410 housing an anode 20b of special configuration. The access from the transfer duct 150 to the anode chamber 410 is covered by a semi-permeable membrane 360 preventing direct contact between the nucleic acids and the anode 20b. A withdrawal chamber 380 underneath the anode chamber 410 communicates with the transfer duct 150, and the pipet tip 290 of a pipetting robot 190 dips into said withdrawal chamber to withdraw the enriched nucleic acids in front of the semi-permeable membrane 360.

The spacer 280 also may be fitted with positioning arms 280e to fix the position of the spacer 280 in the reaction vessel 270, said arms illustratively being laterally braced against the walls 270b of the reaction vessel 270. However it is just as feasible to suspend the spacer 280 by means of these positioning arms 280e from the upper edge of the side wall of the reaction vessel or to clamp them in place there without the spacer touching the base 270a of the reaction vessel 270 by its feet 280c. In this case the reaction vessel is made of a non-conducting plastic and comprises a separate cathode 20a.

The spacer 280 in the embodiment of FIG. 7 illustratively may be removed by the pipetting robot 190, using a robot gripper 400, from a magazine and be configured in the reaction vessel. After depositing the electrically non-conducting spacer 280 in the reaction vessel 270, a corresponding loading of the reaction vessel 270, including the transfer duct 150 and the withdrawal chamber 380, as well as a separate loading of the anode chamber 410, for instance with an electrophoretic buffer solution, may be carried out The gripper 400 need not necessarily be in the form of tongs able to open and close to seize an object. Equally well the gripper 400 may comprise a rigid, fork-like seat, by means of which it moves underneath a corresponding collar of the object before lifting it and thus receiving it.

As already mentioned before, the semi-permeable membrane 360 protects the nucleic acids against direct contact with the anode to prevent electrical discharges from the nucleic acids in the vicinity of the electrode.

Figure 8:
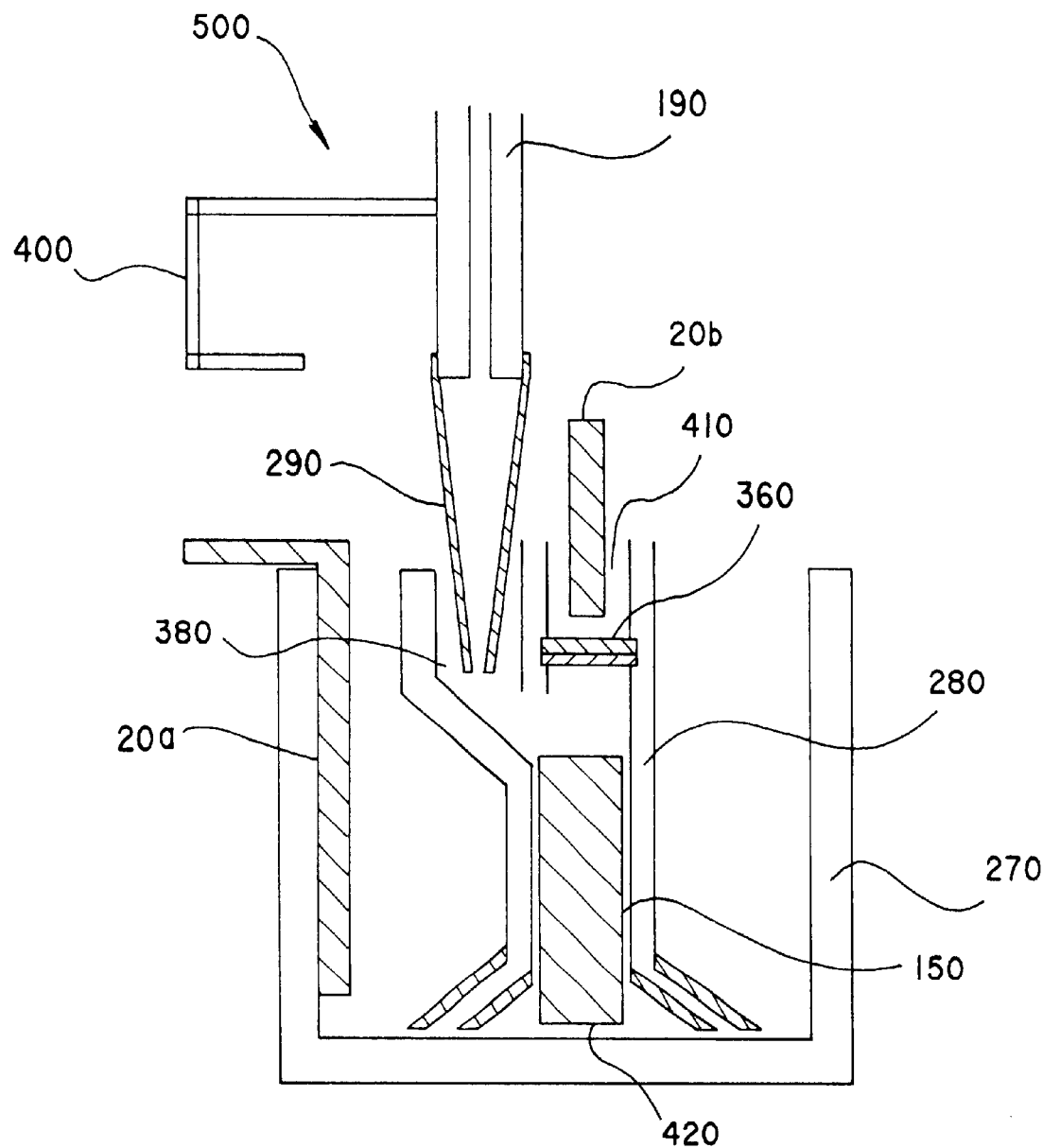

Essentially the embodiment of FIG. 8 corresponds to that of FIG. 7 from which it merely differs in that a gel 420 with which to carry out gel electrophoresis is present in the transfer duct 150. This gel projects downward from the transfer duct 150 and in this manner dips with a large surface into the reaction mixture in the reaction vessel 270. The space above the gel 420 can be loaded with reaction mixture through the withdrawal chamber 380. To reliably preclude throughout the entire inner space of the spacer 280 that gas bubbles should accumulate anywhere, advantageously, and as shown in FIG. 9, the semi-permeable membrane 360 shall not be mounted horizontally but shall assume a given slope relative to the horizontal to allow the gas bubble to escape through the removal chamber 380.

Figure 9:
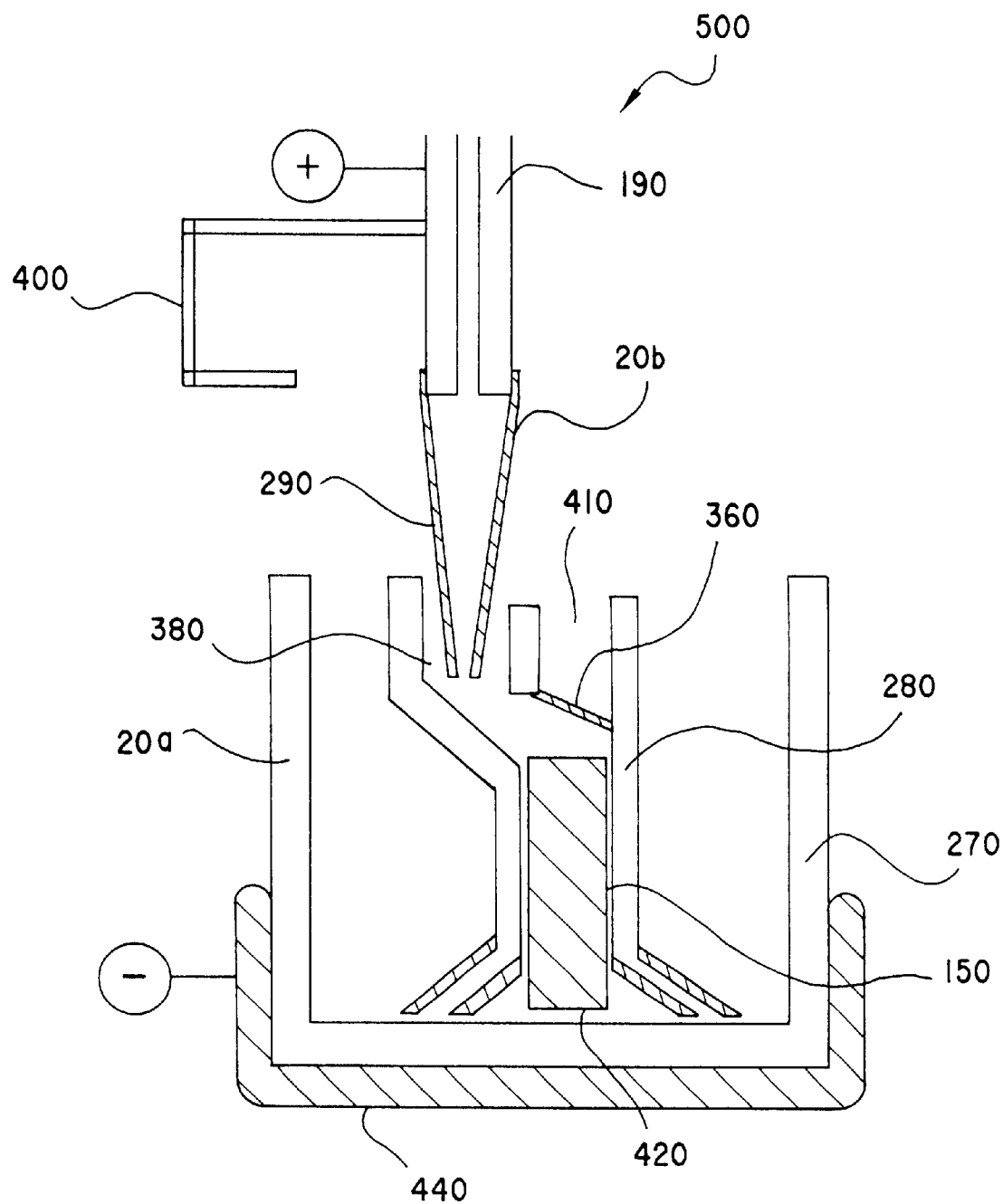

The apparatus 500 shown in FIG. 9 comprises another feature in that a pipet tip 290 made of an electrically conducting plastic is used as the anode 20b. This anode 20b is placed first in the anode chamber 410 to carry out the electrophoresis and following enrichment and turning OFF the voltage is the moved by the pipetting robot 190 into the removal chamber 380 to withdraw the nucleic acids which have accumulated between the membrane 360 and the gel 420.

Moreover the reaction vessel 270 shown in FIG. 9 is made of electrically conducting plastic and mounted in a metallic seat 440.

Figure 10:
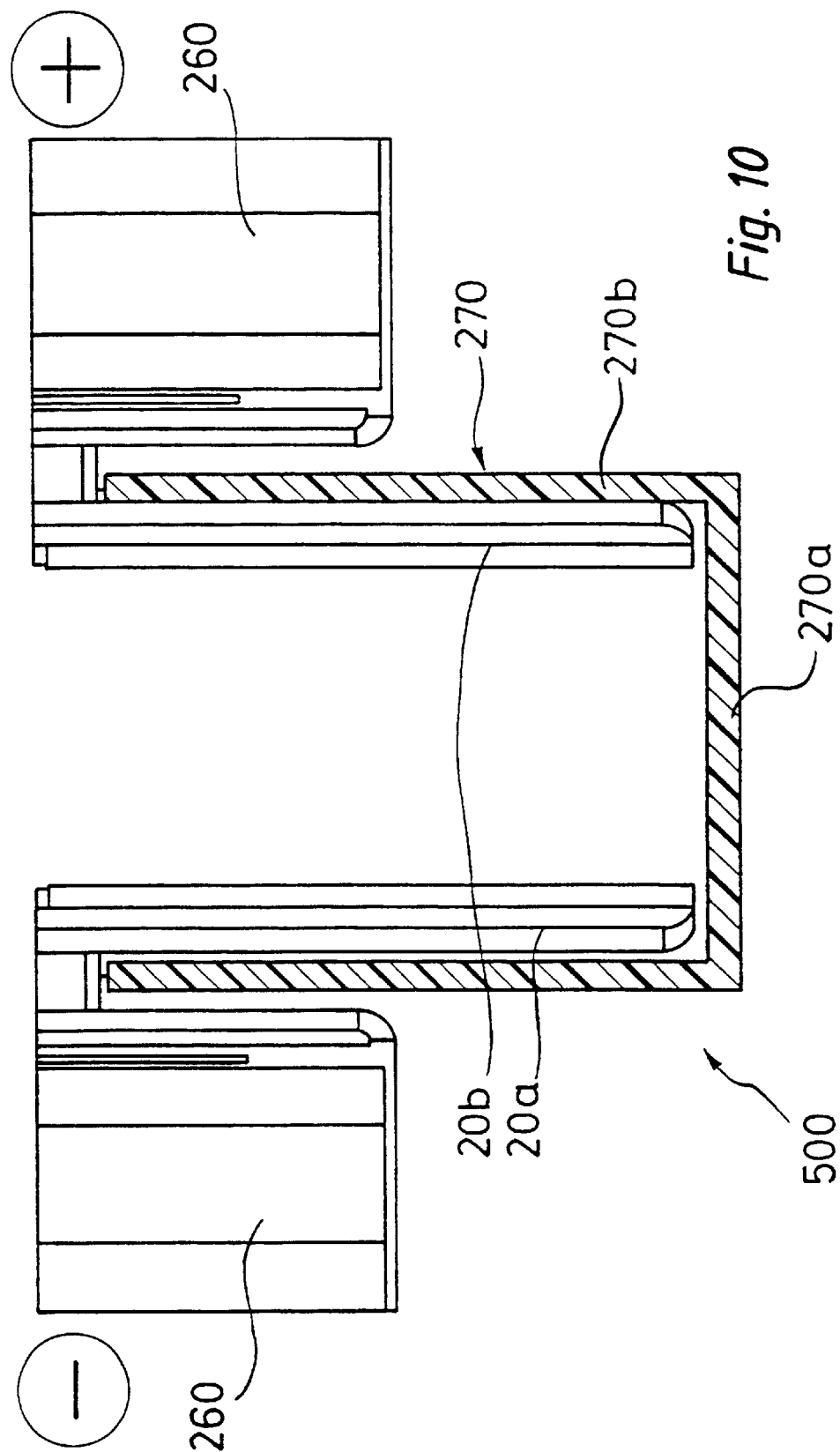

FIG. 10 shows an especially simple embodiment of an apparatus 500 of the invention wherein a non-conducting spacer 280 is not used. A cathode 20a and an anode 20b each with integral electrical terminals 260 are suspended in a reaction vessel 270 fitted with a base 270a free of apertures and side walls 270b also free of apertures. The reaction vessel 270 is made of electrically non-conducting plastic, whereas the electrodes 20a and 20b besides the electrical terminals 260 are made of plastic containing electrically conducting additives. The apparatus 500 of FIG. 10 allows especially economical manufacture and is especially suitable to carry out electrophoretic procedures for which modes a lower process efficiency is acceptable.

Figure 11:
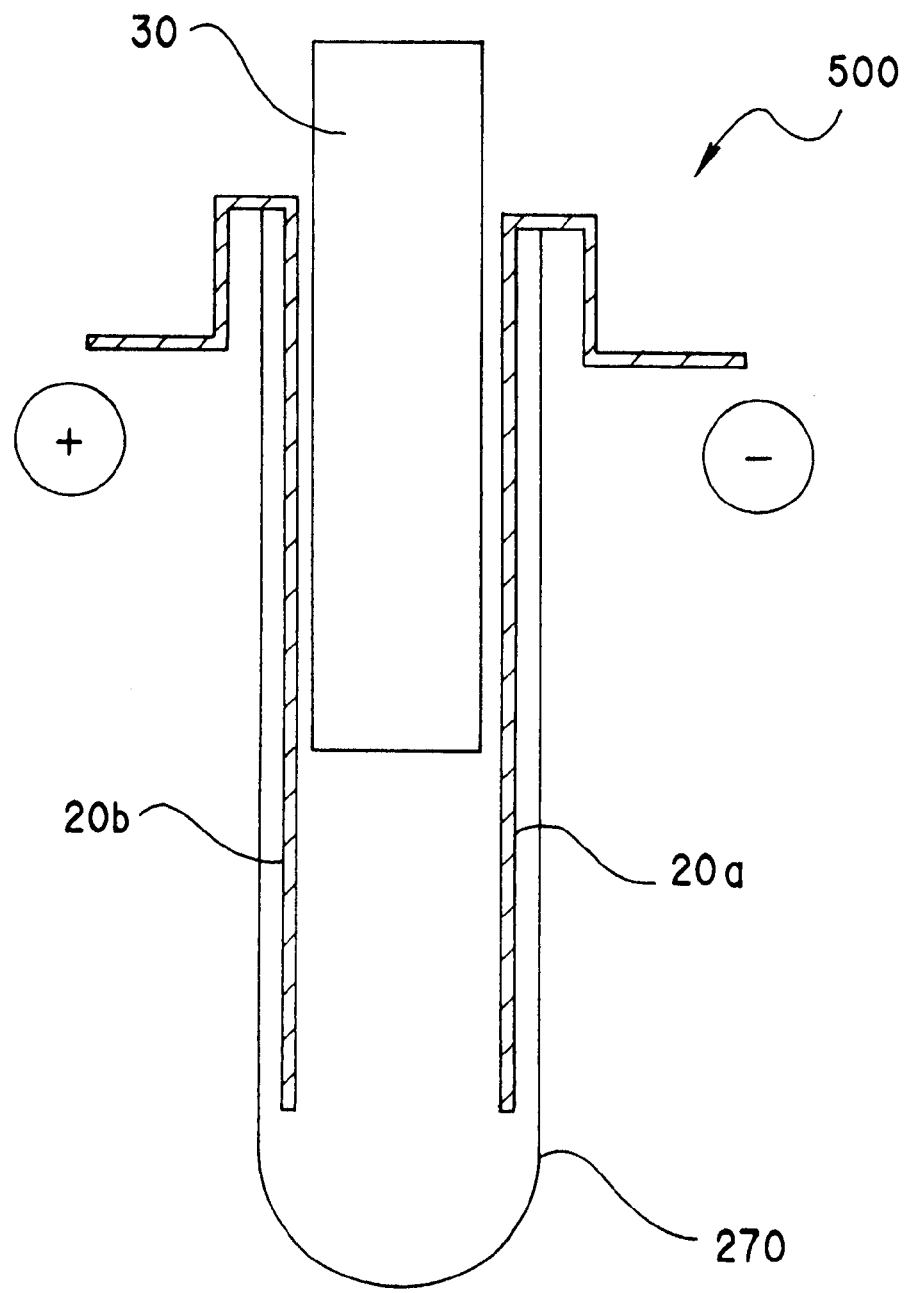

FIG. 11 shows amodified embodiment of the apparatus 500 of FIG. 10 wherein the reaction vessel 270 is designed in the manner of a reactor tube. Bodily contact between the electrodes 20a and 20b is prevented by a spacer 30. Preferably the spacer 30 shall be a hollow cylinder to allow loading the reaction tube 270 through the spacer 30 with reaction mixture or so that the reaction products may be evacuated from the reaction tube by means of a pipet tip passing through the spacer.

Figure 12:
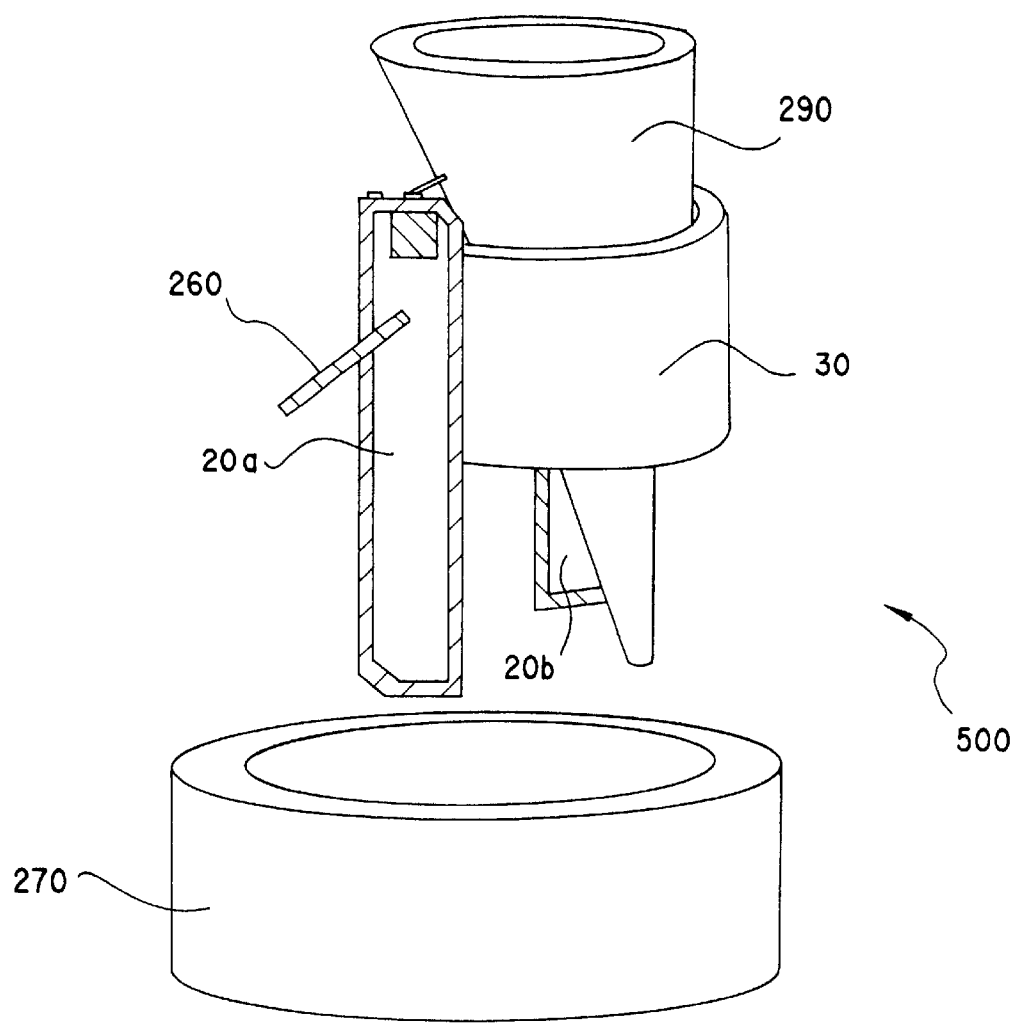
FIG. 12 is a perspective of a further modified embodiment.

A further modified embodiment is shown in FIG. 12. In this apparatus 500 the spacer 30 and the two electrodes 20a and 20b as well as the electrode terminals 260 are one unit. Furthermore the hollow-cylindrical spacer 30 is designed in such a way that it is possible to move a pipet tip 290 through it to evacuate substances from the reaction vessel 270. In a further variation of this embodiment, the pipet tip 290 may be a part of the unit of electrodes and spacer in that it shall be integral with the spacer or shall replace it In the embodiment of FIG. 13 the electrodes 20a and 20b are integrally molded with the reaction vessel 270 made of non-conducting plastic by means of a corresponding localized addition of electrically conducting additives. Magnetic particles 65—more precisely, magnetic particles 65 coated with a special glass to adsorb nucleic acids or the like—are configured in the reaction vessel 270. Following adsorption of the nucleic acids or the like at the magnetic particles 65 and optionally any cleaning steps, the substances adsorbed on the magnetic particles 65 can be detached from them by pulling them electrophoretically toward the anode 20b whereas the magnetic particles 65 are attracted by a magnet 60 toward the cathode 20a. Following substance detachment, these substances may be investigated for instance using a photomultiplier 50 or another appropriate detector.

The magnet 60 in FIG. 13 is composed of a body of permanent magnetic material or of magnetizable material. Electromagnets may be used just as well as shown in simplified, cross-sectional, diagrammatical manner by 60' in FIG. 13a. The permanent magnet 60 in FIG. 13 is shown in its active state, that is a state wherein it is near the reaction vessel 270 and thereby can exert adequate attraction on the magnetic particles 65. To be switched into the inactive state, the magnet 60 only need being moved away from the reaction vessel 270, for instance by relocation, shifting or tipping away. This motion illustratively may be implemented by the pipetting robot 190. In case the electromagnet 60' is used, switching into the inactive state can be implemented by turning OFF the power to the electromagnet 60'.

Figure 14:
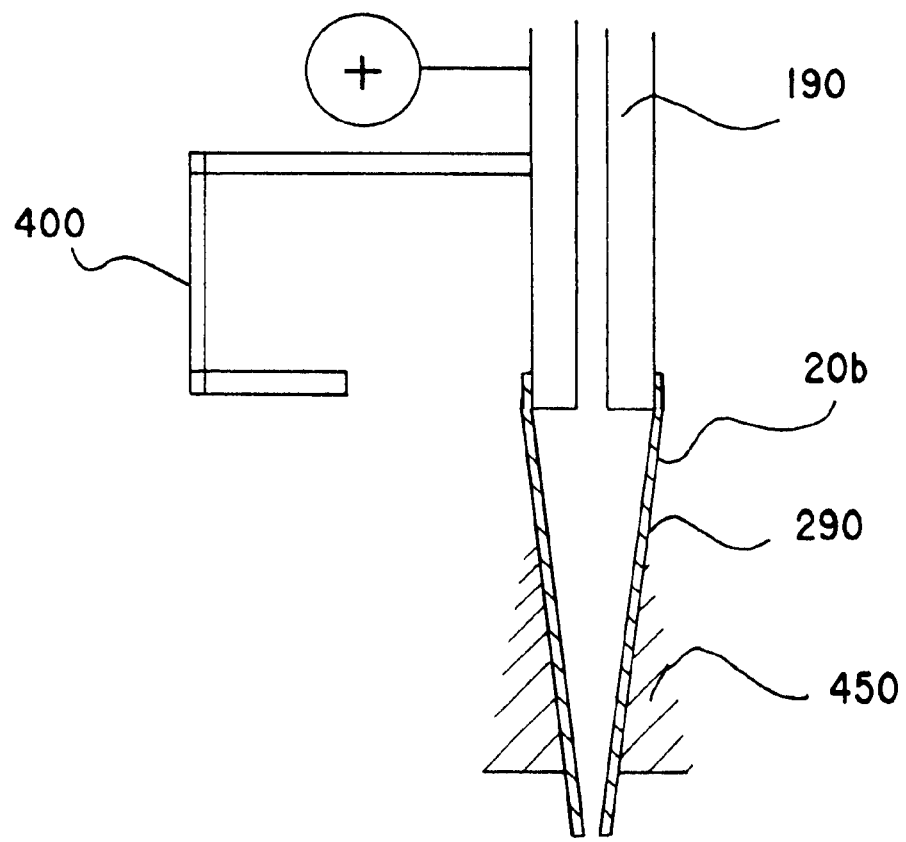
FIGS. 14, 15 are elevations of electrode embodiment variants.

FIG. 14 shows an anode 20b designed as a pipet tip 290. This anode 20b is fitted at its outside with attachments to 450 enlarge the contact area with the reaction mixture and hence to improve the electron current. At the same these attachments 450 may also be used for agitation or mixing purposes.

Figure 15:
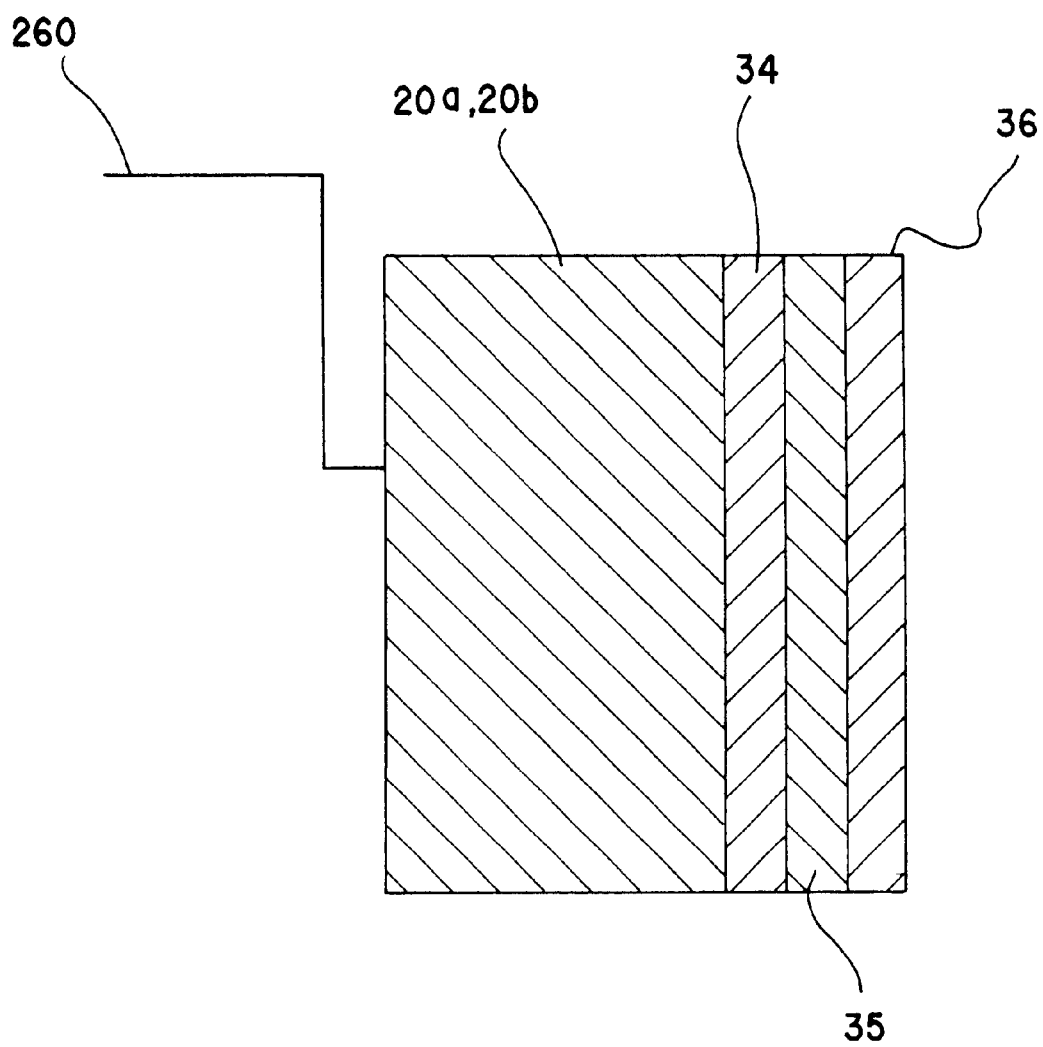

FIG. 15 shows an electrode 20 coated with biological polymers. The coating comprises several layers 34, 35 and 36 to implement appropriate adhesion to the surface of the electrode 20a or 20b. Illustratively the layer 34 may comprise biotinylated bovine serum albumin, the layer 35 may comprise streptavidin or polystreptavidin, and the layer 36 may comprise a biotinylated oligonucleotide. The binding of the oligonucleotide to the electrode 20a or 20b so generated can be utilized in a way that, with the help of the electric field generated between the electrodes 20a and 20b, the hybridization of nucleic acids shall be facilitated or to improve corresponding electrostringency.

The semi-permeable membrane 360 also may be fitted with a corresponding coating. This feature offers the advantage that corrosive chemicals generated by the electrophoretic redox process at the electrode surface cannot interact with the coating because this membrane is configured sufficiently far away. However the electrophoretic current remains directed at the membrane and thereby the desired concentration procedure will take place.

FIGS. 16 and 16a resp. show simplified diagrammatical top and perspective views of a combination structure 550 of apparatus 500 of the invention. The cathode and anodes of these apparatus 500 also shown in simplified schematic manner are connected in parallel by buses 80 and are jointly connected to electrical feed conductors 260. The combination structure 550 comprises a base plate 510 into which are fitted a plurality of receptacles 440. The buses 80 furthermore are imbedded in the base plate 510.

Be it borne in mind that the embodiment of the base plate 510 shown in FIGS. 16 and 16a is especially suitable to receive reaction vessels with integrated cathodes 20a and anodes 20b of the embodiment of FIG. 13. A corresponding combination structure 550 of apparatus 500 however also may be used for the case when the reaction vessels 270 consist of an electrically conducting plastic and thereby form one of the electrodes, preferably the cathode 20a In that case the entire base plate 510 may be made of metal as already discussed above in relation to FIG. 6. If the reaction vessels 270 are made of non-conducting plastic, then a metallic base plate 510 is desirable to implement rapid-response temperature regulation of the reaction mixtures contained in the reaction vessels 270.

The tube units 280 also may be assembled in a corresponding combination structure, preferably into the "96-well" microtitration plate or sub-units derived therefrom, for instance rows each of 8 or of 2×8 tube units. This configuration offers the advantage, in addition to economical manufacture, of simpler and more rapid handling or displacement by means of the robot arm, resulting in a higher sample processing rate. These advantages also apply to a combination structure of pipets or pipet tips.

Figure 17:
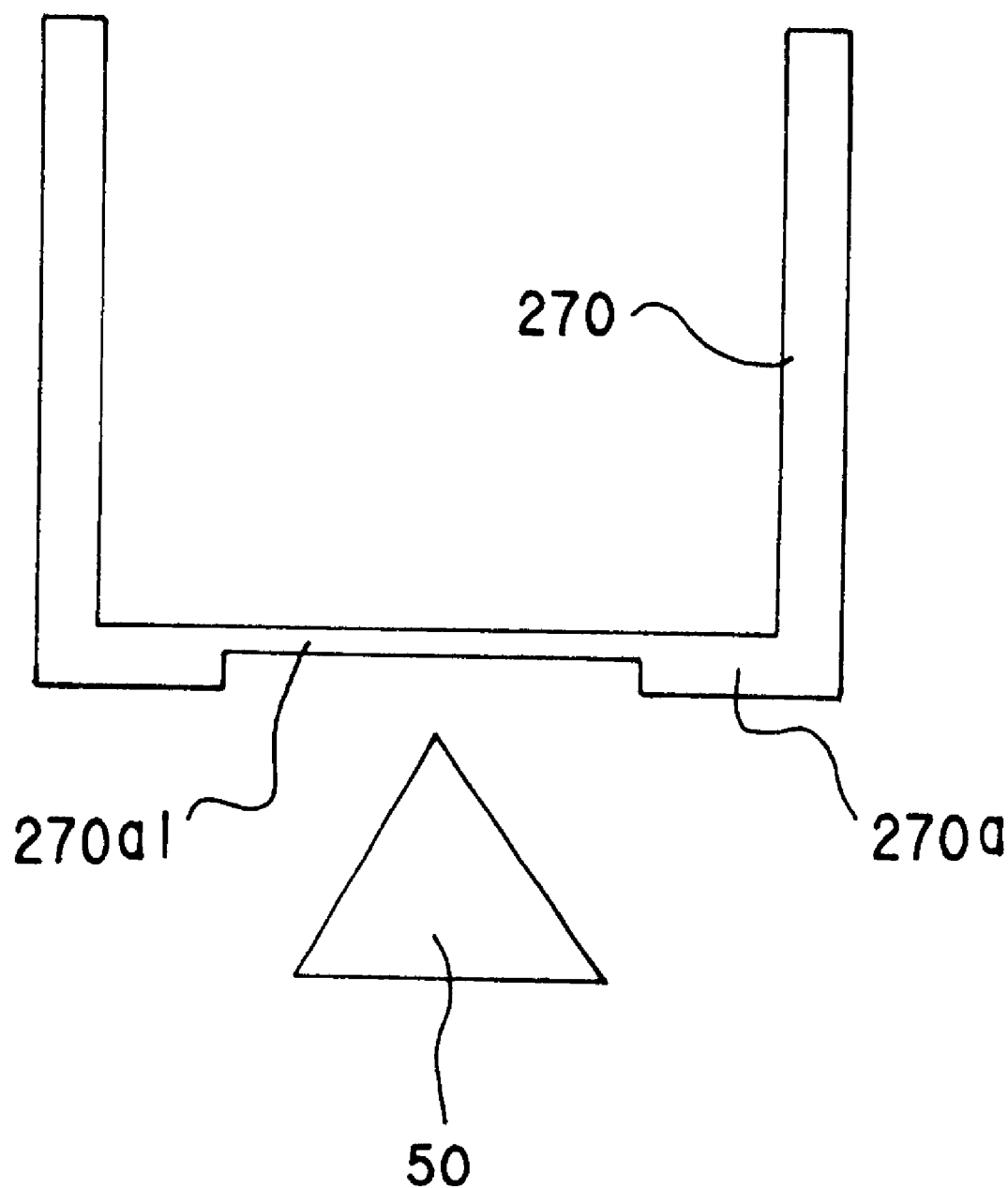

As shown in FIG. 17, the investigation into the substances contained in the reaction vessel 270 can also be carried out, using an appropriate detector 50, for instance a photomultiplier, from the base 270a of the reaction vessel 270. Therefore in FIG. 17 the reaction vessel 270 comprises a zone 270a1 of lesser base thickness. Detection can be carried out in especially problem-free manner in this zone, in particular when using optical detectors.

FIGS. 18 and 19 show embodiments of reaction vessels not part of the present invention. However the snapin lids 90 provided therein, for instance a snap-in lid with an optical window 100 or a snap-in lid 90 with a septum 110 pierced by a needle 120, also are applicable in the apparatus 500 of the invention, namely in the reaction vessels 270 of the invention.

FIG. 20 shows a complete system to carry out nucleic-acid analysis with electro-elution, electro-amplification and electrochemiluminescence detection. This system comprises a pipetting robot 190, a power supply 180, one or more displaceable pennanent magnets 60a and 60b, a photomultiplier 50, a receptacle 200 for the apparatus 500 of the invention, and a rapid-response temperature-regulating system to heat or cool the receptacle 200, such as are known to the expert as temperature cyclers. All these components are computer controlled and allow complete and fully automated nucleic-acid analysis including nucleic-acid isolation, amplification and detection.

Even though FIG. 20 shows an apparatus of FIG. 19 which is not of the invention, it is understood that instead of said apparatus in FIG. 19, the above described apparatus 500 of the invention can immediately be used in the system.

Figure 21A:
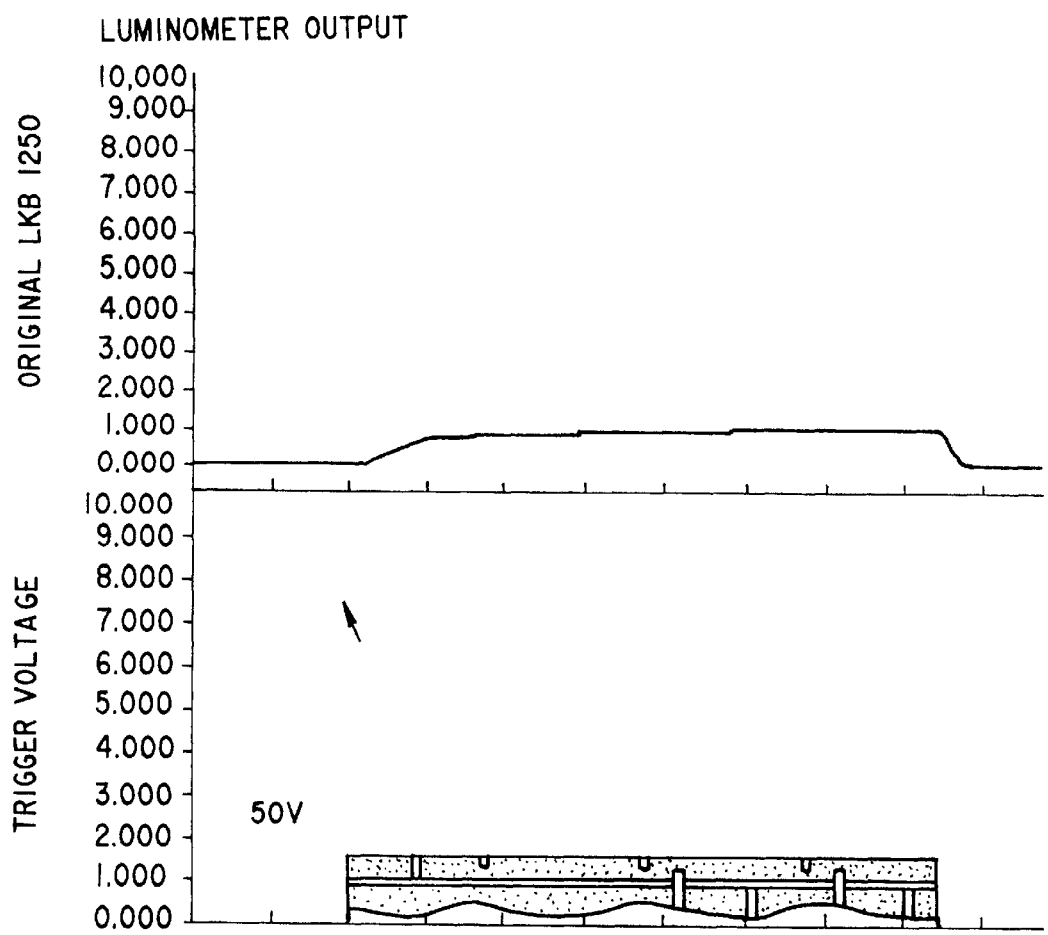
FIGS. 21a, 21b are plots of the results from Example 4.
Figure 21B:
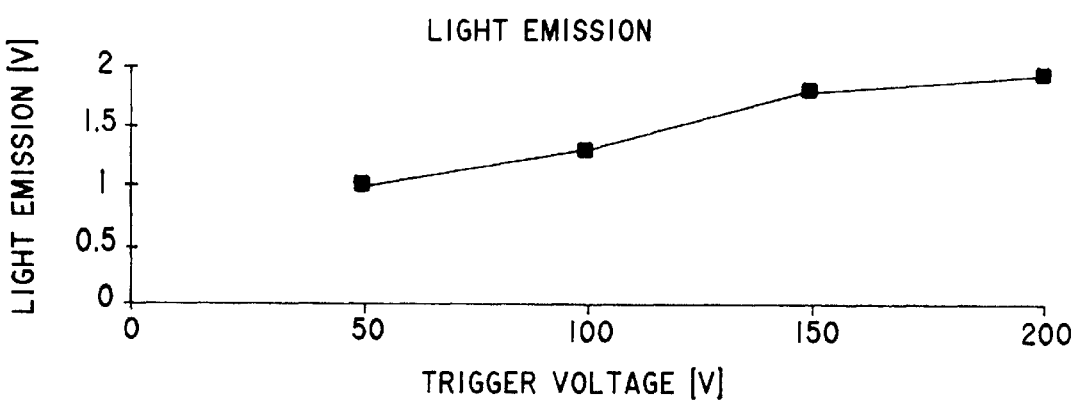

FIGS. 21a and 21b show the test results using electrically conducting pipet tips as the electrodes. The trigger voltage, in this instance 50 v, is shown in the lower part, and the output signal of a luminometer (LKB 1250) at an output voltage of about 1 v is shown in the upper part. FIG. 21b shows the light emission dependency on the trigger voltage when using electrically conducting pipet tips as electrodes.

Polyethylene, polypropylene, polycarbonates, polystyrene or the like may be used as thermally deformable plastics.

Generally implementations using from 1 $\mu$l to 100 $\mu$l are appropriate. Implementations based on reaction volumes up to 100 ml and yielding final volumes of 5 $\mu$l to 50 $\mu$l and therefore of high concentration effectiveness are especially preferred.

The various above discussed embodiments are considered again below with special attention paid to aspects of process-technology:

FIG. 11 shows a is simple apparatus to carry out electrochemiluminescence measurements (Example 3).

FIG. 11 shows a simplified apparatus with a reaction tube 270 and two electrodes 20a, 20b made by injection-molding.

Preferably the reaction tubes are made of such deforming plastic as polyethylene, polypropylene, polycarbonate, polystyrene orthe like and accordingly are electrically non-conducting. The molded body 30 and the reaction tube are made of the same material and said body also is insulating. It acts as a spacer for the electrodes 20a, 20b and, in case the reaction vessel contains no conducting liquid, no electrically conductivity arises between the electrodes. The molded body 30 is cylindrical and hollow, and as a result the reaction tube can be loaded with the reaction solution, for instance for electrochemiluminescence. The electrodes also are made of this material, however they additionally contain electrically conducting additives imparting conductivity to segments of the apparatus. Graphite is preferred as an appropriate additive, however other metallic and electrically conducting particles or substances such as iron, silver, gold, platinum as well as their mixtures or alloys also are suitable. The resistances of the electrodes or conducting segments typically are less than 100 megohms, preferable less than 1 megohm. The resistance may drop when a voltage is applied, without the procedure being thereby degraded. By applying a voltage across the electrodes, biological processes such as electrochemiluminescence for instance may be initiated. Using appropriate test equipment, light emission may be detected as being a signal. Other biochemical processes may be carried out in such apparatus, the above described economical manufacture foremost being suggested for those analytical processes precluding contamination on account of repeat use of the apparatus.

FIG. 15 shows the configuration of a coating of the electrodes of the invention (Example 2).

Hybridizations of nucleic acids are another preferred application. In this regard electrodes coated with biological polymers are advantageously used. Preferably the coating may consist of several layers 34, 35, 36 as shown by FIG. 15 to permit correspondingly strong adhesion to the surface. Illustratively the layer 34 may be a biotinylated bovine serum albumin, layer 35 may be a streptavidin or polystreptavidin and layer 36 may be a biotinylated oligonucleotide.

The binding so produced of the oligonucleotide to the electrode 20 can be exploited to facilitate hybridization by means of the electric field generated by 20a and 20b or to improve the corresponding electrostringency. Such procedures are known to the expert and illustratively are described in the patent documents U.S. Pat. No. 4,478,914; EP 0,331, 127; EP 0,344,578 or U.S. Pat. No. 5,605,662.

FIG. 13 shows an embodiment mode for a simple injection-molded apparatus for electrochemiluminescence measurements.

FIG. 13 shows apparatus of the invention of a reaction vessel 270, preferably in the form of an injection-molded component with integrated electrodes 20a, 20b, a reaction space 275 and an aperture 272 above which is located also for instance a photomultiplier 50 detecting luminescence. Conductive plastics in the form of electrodes 20a, 20b are integrated into the opposite sides though in electrically insulated manner. Illustratively this embodiment also includes a permanent magnet 60 which is moved near in such manner to the electrodes that magnetic particles which for instance bear the ruthenium molecules that are to be detected shall be magnetically attracted to the electrode surface and are excited by an electric trigger into luminescence and shall be detected by the photomultiplier. This integrated design allows economically making this injection-molded part into a disposable item for single use.

FIG. 13a sectionally shows the apparatus of the invention with the electrodes integrated into the molded body and electrically insulated by non-conducting plastics.

Such a device is appropriate for a large number of applications. Illustratively magnetic particles described in the German patent 44 20 732, Example 1a, 1b, which are coated with cell surface antigens to separate a special cell population, may be used in this embodiment mode of the invention. For this purpose the feed of reagents as well as the required washing procedure is made possible through the aperture 272. Thereupon lysing reagents are introduced, preferably in the manner described in the European patent document 0,389,063, which release nucleic acids from cells. By means of electrophoretic forces, which are exerted over the integrated electrodes, the nucleic acids are separated from the magnetic particles. As shown in FIGS. 13 and 13a, this procedure requires configuring the anode 20b opposite the permanent magnet 60, so that the negatively charged nucleic acids shall concentrate in the space in front of the anode while the magnetic particles shall separate at the opposite side.

A comparable application follows from using magnetic particles in the manner disclosed in the German patent 195 20 398. The isolation described therein of nucleic acids is advantageously carried out in apparatus of the invention shown in FIGS. 13 and 13a. Following lysing with chaotropic salts and binding these special magnetic particles to the glass surface, the invention allows implementing detaching the nucleic acids from the surface and hence their elution by using the permanent magnet while at the same time a voltage is applied across the electrodes.

As a result there is enrichment of magnetic particles at the side opposite the anode while the nucleic acids are kept in the space in front of the anode. This process is called "electroelution" based on "Methods in Enzymology 65" pp 371–380 [1980].

FIGS. 16 and 16a show an embodiment of apparatus for the electrochemiluminescence measurement in the form of a simple injection-molding part of the 96-well format of the microtitration plate (top view and perspective view).

FIGS. 16 and 16a show one embodiment mode of this apparatus in the form of a micro-titration plate, wherein the electrodes of the individual bowls are connected in electrically conducting manner with corresponding plastics, as a result of which an electrical terminal to connect to the power supply is present for the whole microtitration plate at two sites and the electrical feed conductors 80 are integrated into the injection-molded part. FIG. 16a shows this configuration from above. This apparatus offers the advantage that the previously described applications can be carried out in this format of microtitration plate.

FIG. 18 shows an embodiment mode of an apparatus combining electroelution and measurement of electrochemiluminescence in the form of a simple injection molded part, in particular as a "closed system" (FIG. 19) reducing contaminations.

FIGS. 18 and 19 show apparatus combining electroelution in a derivative variation and the measurement ofelectrochemiluminescence. This feature of the invention offers the advantage that the two important processes, namely "nucleic-acid isolation" and "nucleic-acid detection" can be carried out in one and the same apparatus. In other words, by minimizing the transfer steps of the reaction liquids, substantial reduction in contamination, that is introduction of undesired nucleic acid from the surroundings, which may lead to spurious analytical results, is made possible.

The molded body 270 of FIG. 18 corresponds to the design of FIG. 13. However said body comprises several apertures 272, 130, 140 partly sealed by snap-in lids 90, screw caps orthe like. A snap-in lid 90 with an optical window 100 is used to seal the aperture 272. On the other hand the aperture 130 is fitted with a snap-in lid 90 comprising a septum 110 which may be pierced by a corresponding needle 120. The aperture 272 preferably is used to load the reaction space 275 with reagents, the aperture 130 to load the reaction space 160 and the aperture 140 to evacuate by aspiration the two reaction spaces 275, 160.

Preferably magnetic particles to isolate nucleic acids are used in the apparatus of FIG. 18. These magnetic particles may be moved by means of the permanent magnet 60 toward the electrode 20a. Then electroelution can be carried outto remove the nucleic acid from these magnetic particles. The nucleic acid migrates through the duct 150 toward the electrode 20b. A corresponding supply of reagents can then take place through the needle 120, for instance for purposes of amplification, whereas solutions likely to be discarded can be aspirated through the duct 140. The entire apparatus must be cyclically heated and cooled to attain amplification, for instance by the polymerase chain reaction process (U.S. Pat. No. 4,683,195).

This procedure preferably is carried out at the apparatus' long sides to attain high heat exchange. Then a second kind of magnetic particles can be added through the needle 120 to bind the nucleic acids to be amplified. Furthermore corresponding buffers may e used to allow thereupon detecting the amplified nucleic acids for instance by electrochemiluminescence. For that purpose the magnet 60 is moved near the corresponding reaction space 160 and as a result these magnetic particles are attracted toward the electrode 20a. Then a corresponding electric trigger can be applied to the integrated electrodes to initiate electrochemiluminescence.

In the invention, an apparatus of FIG. 18 can be manufactured in a binary injection molding procedure in simple and economical manner and as a rule shall be used only once.

FIG. 19 shows a comparable variation. In this design the photomultiplier is situated underneath an optical window 100 covering the region of the reaction space 160 around the electrode 20b. A first displaceable permanent magnet 60b is situated at this electrode. Contrary to the case of FIG. 18, a second permanent magnet 60a for the reaction space 275 is situated at the electrode 20a. The aperture 140 leading to a vacuum pump is used to evacuate used reagents and to supply wash solutions. As already described before, the aperture 130 is fitted with a snap-in lid 90 or the like, and so is the aperture 272. This apparatus allows isolating nucleic acids in the manner previously described. If appropriate magnetic particles are used, the nucleic acid will bind to them; by opening the snap-in lid 90 at the aperture 80, an electroelution buffer can be added. Following application of the permanent magnet, the magnetic particles are attracted to the electrodes 20a and by applying a corresponding voltage to the electrodes 20 the nucleic acid can be detached from a corresponding particle surface and be transferred into the reaction space 160. Instead of magnetic particles, other solid phases may be used, such as membranes preferably made of nylon, nitrocellulose or the like, various papers or non-wovens, foremost with fiberglass contents, non-wovens made 100% of fiberglass or materials with ion-exchange active surfaces. In that case amplification can be carried out by appropriate steps in the reaction chamber 160 around the electrode 20b. The generated amplicons then can be bound by adding an appropriate second kind of magnetic particles through the aperture 130 while the snap-in lid 90 is open. The magnetic particles are attracted to the electrode by resting the permanent magnet 60 against the reaction space 160. When the snap-in lid 90 is open, an exchange of buffers can always take place through the aperture 140. Finally a special electrochemiluminescence buffer must be added to subsequently carry out electrochemiluminescence by applying a voltage to the electrodes 20.

The correspondingly emitted light is detected by the photomultiplier 50 as shown in FIG. 18. This embodiment offers the advantage that the two permanent magnets assure a simple reaction procedure. Furthermore other solid phases may be used, in which case the second permanent magnet at the reactions pace 275 may be eliminated.

Figure 22:
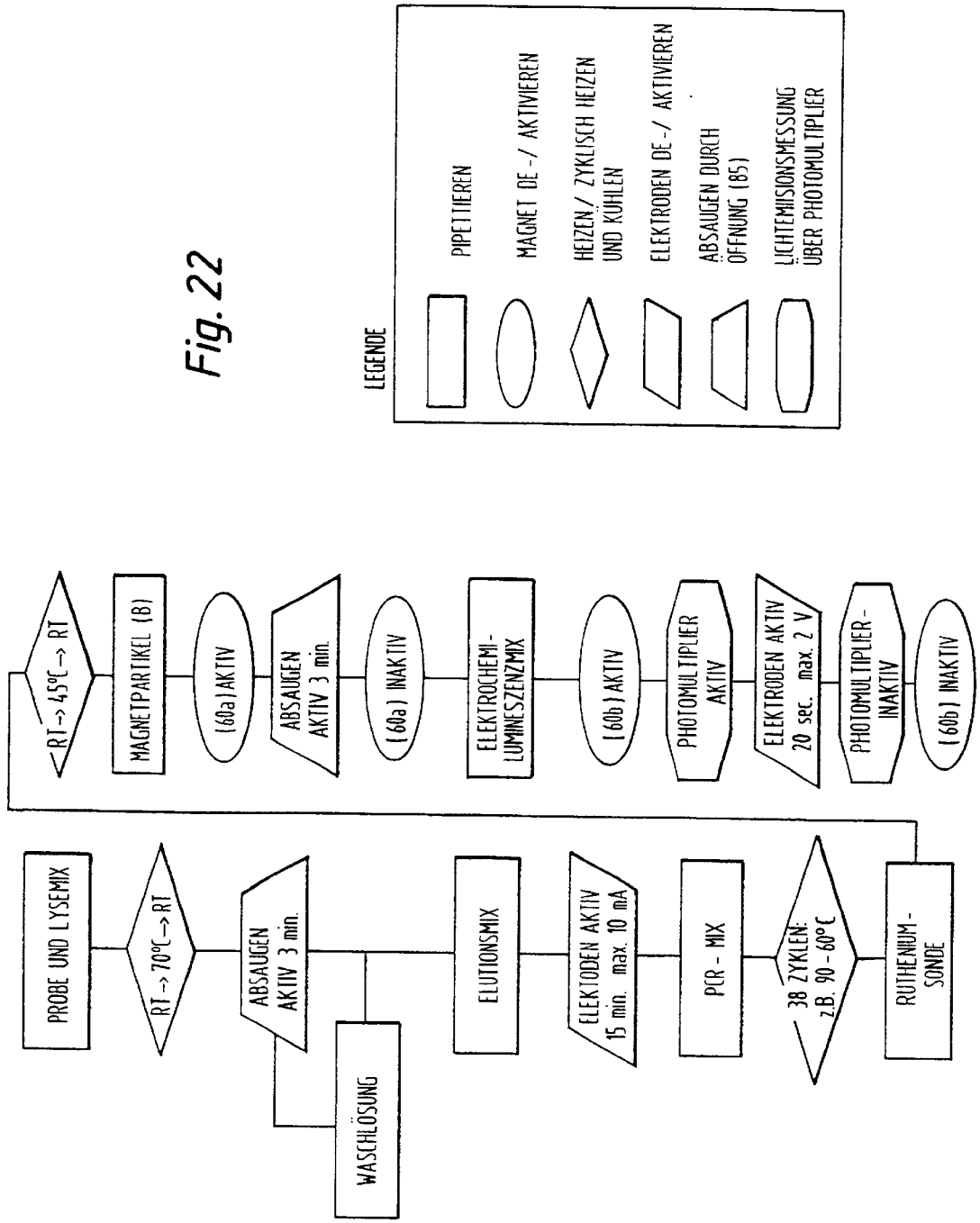
FIG. 22 is a block diagram of a control system for full nucleic-acid analysis using nonwoven fiberglass technology.

FIG. 20 shows a complete system to carry out analysis of nucleic acids using electroelution, amplification and electrochemiluminescence detection. This system is composed of an xyz arm of a pipetting robot 190 (for instance made by TECAN), a power supply 180, a pump 170 to dispose of waste solutions, one or more displaceable permanent magnets 60 or 60a and 60b, a photomultiplier 50 a receptacle 200 receiving the apparatus of the invention such as are illustratively described in to FIGS. 18 and 19, and rapid heating or cooling means for the receptacle 200 such as are foremost known to the expert as temperature cyclers (EP A 0,488, 769). All apparatus modules are operated by a corresponding computerized control and permit complete, fully automated nucleic-acid analysis consisting of isolation, amplification and detection of nucleic acids. A septum-piercing needle is shown in FIG. 18, however procedures to automatically open and closing vessels such as are described in the German patent 44 122 86 and apparatus similar to that shown in FIG. 19, may also be used. Typical procedures are elucidated in Examples 4a and 4b and in the functional diagrams of FIGS. 22 and 23. FIG. 22 shows a functional diagram to control complete nucleic-acid analysis using nonwoven fiberglass technology, whereas FIG. 23 shows a functional diagram to control complete nucleic-acid analysis using magnetic glass particles.

FIGS. 21a and 21b show test results using electrically conducting pipet tips acting as the electrodes 20 from Example 4. In the lower part the trigger voltage in this case is 50 v, the upper part shows the output of a luminometer (LKB 1250) at an output of about 1 v. FIG. 21b shows the dependence of light emission on the trigger voltage when using electrically conducting pipet tips as the electrodes.

The embodiments discussed below share the feature that they can be nested in each other by Cartesian displacement in the xyz direction.

FIG. 1 is a perspective of an embodiment mode of the invention with nesting electrodes in the form of a pipet.

FIG. 1 is an overview summarizing a functional assembly. This assembly consists of a reaction vessel 270, an electrically conducting, cylindrical electrode 250 fitted with pertinent electrical feed conductors 260. In the invention these conductors are made of plastic containing electrically conducting additives. The diameter of the element 250 is selected in such manner that it can be inserted in a contact-less manner into a reaction vessel 270. The element 280 is a non-conducting connector or a transfer duct. This element 280 can be inserted by clamping into the element 260. A further element 290 is clamped into the upper end of the element 280 and consists of plastics containing electrically conducting additives and a corresponding electrical terminal 260. The cylindrical elements also may be fitted with a press fit cone to allow corresponding clamping. It was found in surprising manner that using a conventional xyz pipetting robot, it is possible to assemble an integrated electrode system by first seating the element 290, then the element 280 being made to dock by an appropriate clamping action and thereupon the element 250 being nested in element 280. In this manner one may implement an apparatus with an xyz robot to carry out electrophoretic processes. Following dipping this nested apparatus composed of 290, 280 and 250 into the reaction vessel 270, electrophoresis for instance can be carried out wherein the liquid material is moved from 270 through the cylinder 280 toward the electrode 290. The electrically non-conducting cylinder part 280 again may contain a liquid, though also an electrically conducting gel, so that gel electrophoresis is made possible in this way too. In the invention, this apparatus may be used for electroelution, an adsorbent loaded with nucleic acid being situated in the reaction vessel 270 for instance. By coating with a corresponding electrophoretic buffer and filling the entire apparatus 250, 280 and 290 with electrophoretic buffer, and upon applying a voltage to the electrical conductors 260, the nucleic acid may be transferred from the adsorbent through the three elements in the upper region 280.

Variants of this embodiment are derived below:

FIG. 2 is a perspective of an embodiment with an electrically conductive reaction vessel assuming the function of the cathode.

A reaction vessel 270 is used in FIG. 2 that comprises electrical conductors 260 and is made per se of a plastic with electrically conducting additives. These then represent a cathode. A corresponding electrically non-conducting cylinder part 280 can be for instance be attached by an xyz robot to a cathodic electrode 290 and be dipped into the reaction vessel 270. In this manner electrophoresis of liquids in the reaction vessel 270 can be implemented in that, after a corresponding voltage has been applied across the anodes and cathodes, transfer of molecules takes place through the transfer duct 280 and a correspondingly purified substance is removed at the upper end of 280.

FIG. 1a elucidates a cross-section of such apparatus. The reaction vessel 270 is situated at the lower end and may receive an electrically conducting cylinder part 250 which then illustratively acts as a cathode. A corresponding non-conducting cylinder part 280 is then attached to the cylinder part 250 which in turn is connected directly by an electrically conducting cylinder part 290. In this manner an electrophoretic current can be set up between the cathode 250 and the anode 290 through the transfer duct 150. The transfer duct may be filled with the pertinent liquids or also with appropriate gel. The expression "gel" herein denotes a conventional agarose gel or pertinent polyacrylic amide gels for instance for a preparatory gel electrophoresis.

FIG. 1b shows apparatus comprising an appropriate pipet. The pipet is able to load the cavity of the cylinder part 250 and the transfer duct 150 in case a liquid is kept there. The pipet furthermore is fitted with corresponding receptacles for power terminals able to transfer an electrophoretic voltage to electrical feed conductors 260.

FIG. 3 is a cross-section of a detail of an embodiment acting as a concentrator.

FIG. 3 is a special embodiment of the electrically non-conducting cylinder part 280. It is fitted with an inverted-funnel shape. An appropriate concentration may be achieved in this manner. Nucleic acids for instance at the base of the reaction vessel 270 may be collected underneath the anode 290 in a very small volume. This space may be emptied upward by means of the above described pipet and the corresponding aperture.

FIG. 10 shows a section of a further embodiment of electodes that are clamped to a reaction vessel. This reaction vessel 270 is electrically non-conducting and is entered by two electrodes 20a, 20b with corresponding terminals for the electrical feed conductor 260. The two electrodes are made of plastic with electrically conducting additives and can be clamped to the reaction vessel. In this manner a reaction vessel can implement electrophoretic processes any time at the inside.

FIG. 12 shows a further embodiment comprising an electrically non-conducting reaction vessel 270 and an apparatus consisting of two electrically conducting electrodes 20a, 20b with corresponding terminals 260 and a non-conducting cylindrical element 30 supporting the two electrodes. This cylindrical element 30 is designed in such manner that for instance a pipet tip 290 can be attached to this element. For that purpose the cylindrical shape may be replaced by a corresponding frusto-conical one. Thereupon this apparatus may be moved for instance by an xyz robot into the reaction vessel 270. After a voltage has been applied across the two electrodes, local separation of the reaction mixture may be carried out and, using the pipet tip 290, biological substance can be removed in the immediate vicinity of the corresponding electrode.

FIG. 5 shows apparatus with a conducting reaction vessel and a pipet tip with integrated electrode.

FIG. 5 shows a comparable embodiment. Therein the reaction vessel 270 is made of an electrically conducting plastic, as a result of which the walls may serve as the cathode. An electric feed conductor 260 is provided for that purpose. A special pipet tip 290 dips into said reaction vessel and is fitted at its top part with an integrated plastic containing conducting additives, this tip illustratively serving as anode 20b. In this case the corresponding receptacle for the pipet can be made metallic and act as the electric feed conductor 260. An electrophoretic process may be initiated in this apparatus, following filling the pipet tip with electrophoretic buffer and dipping the tip into the solution of the reaction vessel 270, by applying a voltage across the cathode and the anode 20b by means of the feed conductor of the reaction vessel 270 and the feed conductor 260 of the pipet tip receptacle. Following separation of the biological substance, the pipet tip is removed from the reaction vessel and shelters the desired biological substance in its inner part.

FIG. 6 shows apparatus with a conducting reaction vessel and receptacle and further a pipet tip with integrated electrode.

FIG. 6 illustrates a further detail of the embodiment of the invention wherein the reaction vessel per se consists of an electrically conducting plastic and acts as an electrode. The power is applied through an electrically conducting, preferably metallic receptacle 440. The metallic form offers the advantage of the invention that the reaction vessel can respond rapidly to temperature regulation in a manner important in handling nucleic acids.

FIG. 7 shows apparatus with an element 280, a conducting reaction vessel and a pipet tip with affixed electrode.

As shown in FIG. 7, the cathode 20a enters a reaction vessel made of non-conducting plastic 270 and similarly to the embodiment of FIG. 10 can be attached to the wall. An electrically non-conducting cylindrical part 280 with a pertinent Y branch enters said reaction vessel and rests on the base by means of suitable foot-like elements, for instance in the form of a tripod. The linear continuation of the transfer duct 150 is covered by a semi-permeable membrane 360. A space 410 is present above the semi-permeable membrane and is entered by an electrode 20b for instance acting as the anode. In the invention this electrode is made of a plastic containing electrically conducting additives. A pipet tip 290 enters an evacuation space 380 from which the corresponding materials can be removed from the inside volume of the reaction vessel 270 through the transfer duct 150.

The element 280 can be removed, by an xyz arm of a suitable apparatus 400, from a supply magazine and be moved into the reaction vessel. The apparatus element 400 consists of a fork-like element which may receive the Y element in appropriate manner. After the electrically non-conducting cylinder part 280 has been deposited in the reaction vessel, loading can be carried out both through the feed 380 and the feed 410 which represents a corresponding reaction space 410 above a semi-permeable membrane 360. The semi-permeable membrane 360 is a protective device mounted in front of the electrode and as a result electrical discharges from molecules to be analyzed may be avoided in the vicinity of the electrode. Illustratively the electrode 20b made of electrically conducting plastic is attached by means of a corresponding receptacle against an electrically conducting pipet tip, as a result of which the receptacle of the pipet tip 290 acts as the electrical feed line for the electrode.

FIG. 8 shows apparatus with the elements of FIG. 7, but with preparatory gel.

FIG. 8 shows that the transfer duct 150 can be filled with gel and that in this way gel electrophoresis can be carried out. It is determinant in this respect that the gel project form the transfer duct in order to achieve optimal dipping into the liquid to be analyzed in the reaction vessel. This protrusion is represented by the element 420 in FIG. 8. The feet of the electrically non-conducting cylinder part 280 are not to be construed having a moving function but to be a tripod whereby the air may undergo a corresponding displacement. The air space above the gel 420 can be filled through the withdrawal space 380, the configuration being such that no air bubbles shall be generated underneath the semi-permeable membrane 360. This invention attains this goal in that the membrane 360 is configured not horizontally, but at a slant to the horizontal. The space 410 above the membrane can accordingly be filled with electrophoretic buffer and thereupon an electrode, for instance 20b, that is acting as the anode, can be dipped into said space. After voltage has been applied to the power leads 260, an electrophoretic exchange takes place between the volume of the reaction vessel and the volume 410 above the membrane. As a result biological substance to be analyzed is enriched between the gel 420 and the membrane 360 and subsequently can be removed by means of a suitable pipet 290.

FIG. 9 shows apparatus such as in FIG. 7, however with a conducting reaction vessel and receptacle and also with a pipet tip with integrated electrode.

FIG. 9 shows an especially simple apparatus of the invention wherein an electrically conducting reaction vessel 270 illustratively serves as the cathode. An element 280 in the form of an electrically non-conducting cylinder part with a Y-branch can be moved by the appropriate transfer element 400 into the reaction vessel. The semi-permeable membrane 360 in this instance is a non-horizontally integrated membrane 360 in such a way that air bubbles are avoided underneath it. The withdrawal space 380 can be loaded with the pipet tip in the manner previously discussed, and so can the space above the electrode 410. A gel with an overhang 420 is present in the transfer duct 150, whereby dipping it into the reaction liquid shall not create air bubbles. In this case an electrically conducting pipet tip is simultaneously the electrode which then is dipped into the space above the semi-permeable membrane 410. The receptacle of the pipet tip 290 is made of an electrically conducting material and in this manner can act as the electrical feed conductor to the electrode. A corresponding receptacle for the reaction vessel 440 may be provided in order to electrically feed the matching electrode. Using this apparatus, the following procedure can be carried out in simple manner using a corresponding xyz robot:

| | |
|---|---|
| Initial condition | gel element 280 in rack magazine |
| step 1 | transfer gel element from rack in tube using the transfer device 400 |
| step 2 | fetch conducting pipet tip 290 |
| step 3 | pipet electrophoretic buffer onto membrane 360 |
| step 4 | pipet electrophoretic buffer under membrane 360 through aperture 380 |
| step 5 | dip pipet tip acting as electrode through membrane into space 410 |
| step 6 | guide electrophoresis by applying voltage across electrodes 20a and 20b |
| step 7 | pipet eluate out of space 380 |

FIG. 14 shows a design of the invention of a conducting pipet tip wherein the electron current is improved by widening 450 the outer wall of the pipet tip. At the same this widening also may be used for agitation or mixing.

The following Examples elucidate the implementing modes of the method of the invention.

EXAMPLE 1

Measuring the Conductivity of the Electrodes of the Invention

The electrical conductivity was illustratively measured using conducting pipet tips (Canberra Packard, Dreieich, # 600 0604) or injection-molded blanks of PRE-ELEC TP 4474 material (Premix Oy, Finland) using a digital multimeter (DT-890, Voelkner Elektronik, Brunswick, # 063-823-314).

| Test Results | | |
|---|---|---|
| | Initial resistance | resistance after about 1 min testing time |
| conducting pipet tips | about 18 MΩ | about 50 kΩ |
| blanks | 20 MΩ | about 5 MΩ |

EXAMPLE 2

Coating an Electrically Conducting Plastic

2a Preparing Biotinylated Bovine Immimoglobulin G (R-IgG)

0.5 ml of a R-IgG solution [2 mg R-IgG (Boeluinger Mannheim Cat. No. 1293621103 in 1 ml PBS ($NaH_2PO_4*1H_2O$ 2.76 g/ltr; $Na_2HPO_4*2h_2O$ 3.56 g/ltr; NaCl 8 g/ltr; pH 7.25)] are mixed with 6 μltr D-biotinoyl-amincpronic acid- N-hydroxysuccinlmide ester solution in PBS and DMSO (batch per Biotin Labeling Kit, Boehringer Mannheim Order Nr. 1418165) and agitated for 2.5 h at room temperature on a magnetic stirrer and then are left to stand overnight. The molar ratio of biotin to R-IgG in this batch is 20/1.

2b Coating Electrically Conducting Plastic with Biotinylated R-IgG

A blank prepared by injection molding from PRE-ELEC TP 4474 (Premix Oy, Finland), is cut into disks of 4 mm diameter which are placed in a well of an uncoated microtitration plate and are washed three times in a solution of 0.2 ml coating buffer ($NaHCO_3$, 4.2 g/ltr pH 9.6). Coating is carried out over night by adding 0.2 ml coating buffer and 6 μμ/ltr R-IgG solution (2a).

Next the disks are washed 3 times with 0.25 ml of Milli-Q water each time and then are tested.

As a control, a batch of R-IgG lacking the biotinylation of 2a) is processed under identical concentrations.

2c Binding Tests

To test binding, the disks of 2b) are mixed with 200 µl of a streptavidin-peroxidase conjugate solution (Boehringer Mannheim Catalog Nr. 1089 153; 1/20,000 dilution in PBS) and are incubated for 45 min with agitation. Then the disks are separated by means of a magnet separator (Boehringer Mannheim order # 1,641,794) and the residue is discarded. This procedure is repeated. Thereupon 200 µl of ABTS solution (Boehringer Mannheim Cat. Nr. 1 204 530 and 1 112 422) are incubated 15 min. The disks are removed, the solution is transferred into a microtitration plate (Innova GmbH) and measured at 405 nm.

| Test results | |
| --- | --- |
| Disks with R-IgG biotin | 453 mE |
| Control with R-IgG | 283 mE |

EXAMPLE 3

Measurement of Electrochemiluminescence

Various materials were used for the electrodes 20a, b in an apparatus shown in FIG. 11 where the plastic molded body 10 is a transparent polystyrene tube (37 mm long, 12 mm in diameter) and the spacer 30 is a polypropylene tube (for instance a filter tube from the "High Pure PCR Template Preparation Kit" by Boehringer Mannheim order # 1 796 828, from which the nonwoven was removed. On one hand electrodes made of a platinum/ruthenium alloy wire of 0.5 mm diameter were used, and on the other hand electrodes approximately 3 mm×50 mm in size that were cut by knife from conducting pipet tips (Packard, Order # 6000604).

1 ml of a buffer containing tripropylamine such as the Boehringer Mannheim Pro Cell buffer for the Elecsy product line (Order # 166 2988) were mixed with 5 µltr of a saturated solution of tris-(2,2'-bipyridyl)ruthenium(II) chloride hexahydrate (Sigma-Aldrich # 93397 Fluka) and converted into (1). The apparatus was placed into the sample chamber of an LKB 1250 Luminometer, two electric feed wires being pulled through extant apertures into the sample chamber. The apparatus was further modified in that the last amplifier stage (IC 7) was bypassed, resulting in smaller test signals. The test signals were detected by a Digital Multimeter (DT 890, Voelkner Elektronik, Brunswick # 063 823 314). The electrode voltage source was an electrophoresis transformer (Hoelzel, Dorfen, # 0 628/1985). The luminometer was calibrated using the internal standard and following the manual. The mixture of reagents at the platinum electrode was observed foaming very strongly.

| TEST RESULTS | | | |
| --- | --- | --- | --- |
| | Trigger voltage V | Relative light intensity (mv) | Test voltage at internal standard |
| Platinum electrodes | about 10 v | max. 1,200 | 1 |
| Electrodes made of conducting plastic | about 10 v | max. 7 | 6 |

In a variation, the voltage source for the plastic electrodes was the electrophoresis transformer cited above (Hoelzel, Dorfen, #0 628/1985) and the voltage source for the platinum electrodes was a power pack made by Voltcraft (NG-500, order # B518034) with a voltage divider and a voltage dropping resistor of 480 Ω to prevent foaming. The luminometer was calibrated using the internal standard and following the manual, the particular test values are each indicated.

| TEST RESULTS | | | |
| --- | --- | --- | --- |
| | Trigger voltage (v) | Trigger current (ma) | Relative light intensity (mv) | test voltage at internal standard (mv) |
| Pt electrodes | 3.25 | 1.1 | max. 5,000 | 1 |
| Conducting plastic electrodes | 25 | 0.175 | max. 25 | 6 |
| | 6.5 | 0.007 | max. 7 | 6 |

In a third detection variation, the luminometer was modified in that the last amplifier stage (IC 7) was bypassed, entailing test signals smaller by about a factor of 10. The test signals were directly entered in a computer by means of a µM 4 measurement module (analog converter BMC Systeme GmbH, from Conrad Elektronic order # 10 75 57-99), the trigger voltage and the light emission in the form of the huninometer output also being stored simultaneously. The voltage source for the plastic electrodes was an electrophoresis transformer (Hoelzel, Dorfen, # 0628/1985) and for the platinum electrodes it was a power pack (NG 500 Voltcraft, order # B5 18034) with a voltage divider and a voltage dropping resistor of 480 Ω to prevent foaming. The luminometer was calibrated using the internal standard and following the manual. When using the electrophoresis transformer and the analogue converter voltage divider input voltage of 10 v was generated.

FIG. 21a is a plot of the test signal of the luminometer and of the trigger voltage. FIG. 21b shows the dependency of the test signal on the trigger voltage.

EXAMPLE 4a

Implementing Full Analysis of Nucleic Acids with Sample Preparation, Amplification and Measurement of Electrochemiluminescence Using Glass Nonwoven Technology by Illustrating the Detection of the Hepatitis C Virus This operation is based on apparatus shown in FIG. 19 though with only one permanent magnet 60b in the immediate vicinity of the photomultiplier 50, and on the control function shown in FIG. 2. A glass nonwoven is situated above the aperture 140 and was obtained from the QIAamp-Blood kit (cat # 29104) of Qiagen (Hilden). All associated reagents from this kit used for sample preparation were used as follows:

200 µltr plasma were lysed following the accompanying instructions and bound to the glass nonwoven, all centrifugation operations being replaced by aspirating with a membrane pump 4151 (made by Eppendorf) through the aperture 140. 300 µltr of an electrophoretic buffer prepared in the manner of A T Andrews Electrophoresis, Clarendon Press, Oxford, 1986, p 160) were used. The electrodes 20a, b were wires of a platinum-ruthenium alloy of 3 mm diameter and the voltage source was the electrophoresis voltage source made by Hoelzel, Dorfen.

All the reagents of the HCV Amplicore Kit made by Hoffinann LaRoche (#075 3912,075 3890, 075 3904) were used for amplification. This kit employs a biotinylated primer. The batch described by KKY Young et al in Journal of Microbiology 1993, pp 882–886 was appropriately adapted.

Thereupon 50 µltr of a corresponding amplification mix comprising HCV-specific primers was added by pipetting through the aperture 130, a corresponding 7-fold concentration by the residual volume of about 300 µltr for the individual concentrations were taken into account. Thereupon the temperature cycling routine described in the operations for use for RT-PCR was applied.

Next an HCV specific probe (nt 251–275) made in the manner of KKY Young et al (ibid) able to hybridize with the amplificate was added by pipetting through the aperture 140, the probe being labeled with ruthenium. The temperature is raised to 45° C. and cooling to room temperature is implemented to melt the double strand and the hybridization with the probes. Thereupon 50 µltr streptavidin coated magnetic particles are added (Boehringer Mannheim order # 1 641 778) and are incubated for 15 min at 37° C. Next the permanent magnet 60b was activated and all the solution of reaction was aspirated through the aperture 140. Thereafter 300 µltr of a buffer containing tripropylamine (Boehringer Mannheim Pro Cell buffer for the Elecsys product line order # 166 2988) was added by pipetting through the aperture 130 and a trigger voltage of 3.5 v was applied to the electrodes 20a or 20b. The emitted light was measured by a photomultiplier as in Example 3.

EXAMPLE 4B

Carrying Out a Complete Nucleic-acid Analysis with Sample Preparation, Amplification and Electrochemiluminescence Measurement Using Glass Particles for an Example Detecting the Hepatitis C Virus This example uses the apparatus of FIG. 19 with two permanent magnets 60a, b and the control function of FIG. 23.

All reagents are taken from the High Pure PCR template Preparation Kit of Boehringer Mannheim (order# 1 796 828). The glass magnetic particles are made by Merck, Darmstadt (order # 1.01193.0001). 200 µltr plasma were lysed according to accompanying instructions and bound to 50 µltr suspension of glass magnetic particles. Next the magnet 60a was activated and the lysing mixture was removed by evacuation using a membrane pump (made by Eppendorf, 4151) through the aperture 140. The ensuing washing steps were carried out similarly.

The ensuing electroelution and all other steps of further processing including detection were carried out as in Example 4a.

What is claimed is:

1. An apparatus to isolate and enrich charged molecules, comprising:
    a plastic vessel defining a receiving chamber that receives a reaction mixture having at least one of a sample containing the charged molecules and reagents, said receiving chamber having an upper access aperture being externally accessible;
    a tube unit made of an electrically non-conducting plastic positioned within said receiving chamber, said tube unit having an open upper end and an open lower end opposite said open upper end, an inner surface of said tube unit contacting said reaction mixture in said receiving chamber wherein said tube unit is positioned inside the receiving chamber of said vessel through said upper access aperture,
    a withdrawal chamber and an electrode chamber located within said open upper end of said tube unit, said withdrawal chamber and said electrode chamber being separate from and adjacent to each other, said open upper end of said tube unit communicating with said open lower end of said tube unit by an internal chamber;
    a first electrode positioned within the receiving chamber and contactable with the reaction mixture inside the receiving chamber and outside the tube unit, and a second electrode positioned within said electrode chamber; and
    a semi-permeable membrane located at a lower end of said electrode chamber that prevents direct contact between the charged molecules and said second electrode.

2. The apparatus as claimed in claim 1, wherein the tube unit is deposited on a base of the vessel.

3. The apparatus as claimed in claim 1, wherein the tube unit comprises positioning arms that stabilize a position of the tube unit in the vessel.

4. The apparatus as claimed in claim 1, wherein a gel material is provided in the internal chamber of the tube unit and extends completely across an interior width of said tube unit.

5. The apparatus as claimed in claim 1, wherein the tube unit flares away from the second electrode in a direction toward a base of the vessel.

6. The apparatus as claimed in claim 1, wherein at least one of the first and second electrodes is made of a plastic comprising electrically conducting additives.

7. The apparatus as claimed in claim 1, wherein at least one of the first and second electrodes is a separate element from the vessel.

8. The apparatus as claimed in claim 1, wherein at least one of the first and second electrodes is designed as either one of a pipet tip and a part of a pipet tip.

9. The apparatus as claimed in claim 1, further comprisina attachments that are either mounted on an exterior of the second electrode or integrated with the exterior of the second electrode.

10. The apparatus as claimed in claim 1, wherein at least one of the first and second electrodes is integral with a wall of the vessel.

11. The apparatus as claimed claim 1, wherein at least one of the first electrode, the second electrode, and the semi-permeable membrane is provided with a coating.

12. The apparatus as claimed in claim 11, wherein the coating comprises several layers.

13. The apparatus as claimed in claim 11, wherein the coating includes at least one biological polymer.

14. The apparatus as claimed in claim 13, wherein the biological polymer is able to bind a nucleic acid.

15. The apparatus as claimed in claim 1, wherein adsorbents are either present in the vessel or directed into the vessel to separate the charged molecules.

16. The apparatus as claimed in claim 15, wherein the adsorbents include at least one of a silica gel, and an agarose gel, and a polyacrylic amide gel, and an ion-exchanger substance, and a fiberglass nonwovens, and glass particles, and glass enclosed magnetic particles.

17. The apparatus as claimed in claim 1, wherein a magnetic field source associated with the vessel and can be transferred between an active state wherein the magnetic field source exerts an attractive force on magnetic particles present in the vessel and an inactive state wherein magnetic field source exerts substantially little or no force on the magnetic particles.

18. The apparatus as claimed in claim 17, wherein the magnetic field source comprises an electromagnet.

19. The apparatus as claimed in claim 1, further comprising a pipetting robot.

20. The apparatus as claimed in claim 17, wherein a pipetting robot and the magnetic field source are integrated so that the pipetting robot is able to manipulate the magnetic field source between the active and inactive states.

21. The apparatus as claimed in claim 19, wherein the pipetting robot includes a gripper.

22. A combination structure of the apparatus as claimed in claim 1, wherein the second electrodes of the apparatus are interconnected, the first electrodes of the apparatus are interconnected, and a plurality of the vessels are combined into a microtitration plate.

23. A method to isolate and/or analyze charged molecules, by adsorbing charged molecules in solution to an appropriate adsorbent, by separating the remaining solution and optionally washing the adsorbent, detaching the molecules from the adsorbent and separating the molecules, wherein the method is carried out in an apparatus as claimed in claim 1, the apparatus being used to contain the adsorbent, or an absorbent previously loaded with charged molecules being introduced into the apparatus and wherein detachment of the molecules from the adsorbent is implemented by electroelution.

24. A method to isolate and/or analyze charged molecules by depositing a sample comprising the charged molecules on a separation gel and by electrophoretically separating the charged molecules based on different molecular weights, wherein the method is carried out in an apparatus as claimed in claim 1, the apparatus comprising a separation gel introduced into the apparatus before the sample is deposited.

25. A method to isolate and/or analyze charged molecules by adsorbing the charged molecules in solution to an appropriate adsorbent, by separating the remaining solution and optionally washing the adsorbent, detaching the molecules from the adsorbent and separating the molecules, wherein the method is carried out in a combination structure as claimed in claim 22, the combination structure being used to contain the adsorbent, or an absorbent already loaded with charged molecules being introduced into the combination structure, and wherein at least the detachment of the charged molecules from the adsorbent is implemented by electroelution.

26. A method to isolate and/or analyze charged molecules by depositing a sample comprising the charged molecules on a separation gel, and by electrophoreuically separating the charged molecules based on different molecular weights, wherein the method is carried out in a combination structure as claimed in claim 22, the combination structure comprising a separation gel introduced into the combination structure before the sample is deposited.

\* \* \* \* \*

UNITED STATES PATENT AND TRADEMARK OFFICE
CERTIFICATE OF CORRECTION

PATENT NO.    : 6,264,814 B1
DATED         : July 24, 2001
INVENTOR(S)   : Hans Lange It is certified that error appears in the above-identified patent and that said Letters Patent is hereby corrected as shown below:

<u>Title page,</u>
Item [73], Assignee, please change Assignee's name from:

"BILATEC Gesellschaft zur Entwicklung"
                To:
-- BILATEC Gesellschaft zur Entwicklung
   biotechnologischer Systeme mbH --

Signed and Sealed this

Eighteenth Day of June, 2002

Attest:

JAMES E. ROGAN
Attesting Officer        Director of the United States Patent and Trademark Office